United States Patent
Takada et al.

(10) Patent No.: US 6,266,983 B1
(45) Date of Patent: Jul. 31, 2001

(54) METHOD AND APPARATUS FOR DETECTING FLAWS IN STRIP, METHOD OF MANUFACTURING COLD-ROLLED STEEL SHEET AND PICKLING EQUIPMENT FOR HOT-ROLLED STEEL STRIP

(75) Inventors: Hajime Takada; Toshihiro Sasaki; Masato Iri; Makoto Aratani; Hideo Kuguminato; Hidenori Miyake; Masuto Shimizu, all of Chiba; Susumu Okada, Chiyoda-ku; Yasuo Tomura, Chiba, all of (JP)

(73) Assignee: Kawasaki Steel Corporation, Kobe (JP)

( * ) Notice: Subject to any disclaimer, the term of this patent is extended or adjusted under 35 U.S.C. 154(b) by 0 days.

(21) Appl. No.: 09/447,553

(22) Filed: Nov. 23, 1999

(30) Foreign Application Priority Data

Dec. 9, 1998 (JP) .................................................. 10-350150
Dec. 9, 1998 (JP) .................................................. 10-350151

(51) Int. Cl.[7] .................................................. B21B 37/00
(52) U.S. Cl. .................................. 72/11.1; 72/8.3; 72/38; 73/600; 73/620; 73/624
(58) Field of Search .............................. 72/11.1, 7.4, 8.3, 72/8.8, 11.2, 11.5, 38, 365.2; 73/599, 600, 620, 622, 624, 629

(56) References Cited

U.S. PATENT DOCUMENTS 4,117,732 * 10/1978 Brazhnikov .............................. 73/599
4,292,847 * 10/1981 Tait ........................................ 73/587
4,562,737 * 1/1986 Davies .................................... 73/622
4,893,510 * 1/1990 Ichikawa et al. ...................... 73/620
5,165,280 * 11/1992 Sternberg et al. ..................... 73/622

FOREIGN PATENT DOCUMENTS

| 60-78345 | 5/1985 | (JP) . |
| 5-149929 | 6/1993 | (JP) . |
| 7-113795 | 5/1995 | (JP) . |
| 7-253414 | 10/1995 | (JP) . |
| 8-184537 | 7/1996 | (JP) . |
| 10-185902 | 7/1998 | (JP) . |
| 11-83815 | 3/1999 | (JP) . |

* cited by examiner

*Primary Examiner*—Ed Tolan
(74) *Attorney, Agent, or Firm*—Oliff & Berridge, PLC

(57) ABSTRACT

A flaw detecting method and apparatus for continuously testing a strip that is continuously carried through a liquid includes features for reducing air bubble generation in a liquid. The apparatus includes a liquid, carrying rolls for passage of the strip through the liquid, and ultrasonic testing probes arranged in the liquid for testing the strip. A carrying roll in contact with the liquid is fully immersed. Air bubble generation is inhibited to improve the testing reliability by at least one of (a) shielding the liquid dropping from the portion of the strip leaving the liquid, (b) reducing the dropping force of the liquid onto the liquid surface by inclining the strip, (c) installing the fully immersed carrying roll at a depth of at least 5 mm in the liquid, and (d) using a carrying speed of less than about 200 m/min. Upon manufacturing steel strips, testing is carried out in the stage of hot-rolled steel sheet, or, preferably, in pickling equipment.

20 Claims, 10 Drawing Sheets

| KIND | PROPERTIES OF INCLUSIONS | SHAPE IN SLAB | SHAPE AFTER HOT ROLLING |
|---|---|---|---|
| A | SPHERICAL OR ANGULAR, LUMPY, HIGH-MELTING-POINT, EXTRA-HARD, FINE INCLUSIONS<br><br>Al₂O₃<br>Al₂O₃ CLUSTER (SLIVER) |  |  |
| B | OVAL, MEDIUM-MELTING-POINT, MEDIUM-SIZED HARD INCLUSIONS<br><br>CaO-Al₂O₃ |  |  |
| C | TORN IN SEVERAL PIECES, LOW-MELTING-POINT, COARSE, RATHER SOFT INCLUSIONS<br><br>CaO-SiO₂-Al₂O₃-Na₂O |  |  |

METHOD AND APPARATUS FOR DETECTING FLAWS IN STRIP, METHOD OF MANUFACTURING COLD-ROLLED STEEL SHEET AND PICKLING EQUIPMENT FOR HOT-ROLLED STEEL STRIP

BACKGROUND OF THE INVENTION

1. Field of Invention

This invention relates to a flaw detecting method and an apparatus therefor suitable for detecting flaws in a strip while being carried.

Further, this invention relates to the manufacture of a hot-rolled sheet or a cold-rolled sheet, and, in particular, an inspecting method and a manufacturing method of a sheet. This invention also relates to a manufacturing equipment for a sheet.

2. Description of Related Art

In the area of manufacture and working of metallic and nonmetallic strips such as steel strips, there is a demand for a technique of online detection of flaws contained in strips to achieve quality control and quality assurance. The need is particularly for an apparatus capable of detection of internal fine flaws, and such an apparatus is generally known as a testing apparatus.

There is an another technique comprising, analyzing a specimen sampled from rolled steel strip, estimating the quality level of whole steel strip on the basis of the results of analysis, as disclosed in Japanese Unexamined Patent Publication NO. 08-184537 and NO. 10-185902. However, these techniques have no reliability in their application to the evaluation of steel strip with few internal flaws such as steel strip for cans, because the probability of sampling of internal flaws is extremely low.

Testing apparatus capable of continuously testing over the entire volume of a strip (such as a steel strip) that is carried continuously mainly include testing apparatus based on the magnetic leakage flux testing technique and testing apparatus utilizing ultrasounds.

The magnetic leakage flux testing technique comprises magnetizing a strip (typically a ferromagnetic metallic strip) by a magnetizing device and detecting leakage of the magnetic flux caused by flaws using a magneto-sensitive element such as a Hall-effect element, coil, or magnetic diode.

It is, however, impossible to test a strip having a thickness of over approximately 0.5 mm by the magnetic leakage flux testing technique. For a strip having a thickness as large as that of a hot-rolled steel sheet, the ratio (flaw cross-sectional area/steel sheet cross-sectional area) becomes smaller, and this makes it difficult for the magnetic flux to leak to the surface.

The magnetic leakage flux is rapidly attenuated in inverse proportion to the distance from the strip surface. It is therefore necessary to control upward and downward fluctuations of the strip pass-line within ±0.1 mm, and limit the gap between the detecting head and the strip surface within 0.5 mm. Because of the necessity of such a strict gap control, it is difficult to continuously and stably test the strip in transfer. Particularly, at a high carrying speed of the strip, the gap control is more difficult.

Another problem of the magnetic leakage flux testing technique is that a false detection can easily occur because of many noise factors. The magnetic leakage flux testing technique has a further limitation that is impossible to obtain accurate information of the shape of a detected flaw.

The ultrasonic testing technique comprises applying ultrasounds into a strip, thereby detecting reflection or shadow caused by internal flaws. Because it is possible to provide a large gap between the strip surface and the detecting head as compared to the magnetic leakage flux testing method, and detect flaws even in a thick strip, the ultrasonic testing technique is considered more suitable for the continuous testing of general strips.

There is also known a contacting ultrasonic testing technique known as the lamb wave testing technique. This technique is based on the detection propagating the lamb wave in the width direction of the strip through rolling contact of a wheel search unit (detecting head) with the strip surface. A disadvantage of this technique is its low detectability and the presence of a dead zone in the strip thickness direction. Further, it is practically impossible to test a wide range of the strip continuously in high speed transfer.

Because the lamb wave testing technique is a contact type technique, the probe may sometimes become bound and further, the medium between wheel search unit and the strip cannot be stably supplied at high transfer speeds of the strip. Thus, the carrying speed of the strip is limited within a low range. The lamb wave testing technique has another risk of bursting of the wheel.

An immersion (or soak or dip) testing technique, such as water immersion testing, is a non-contact testing technique and is free from the problems as described above. That is, there is available an advantage of a slight effect of fluctuations of the pass-line upon transfer of the strip.

For immersion testing using ultrasounds for the propose of detecting flaws such as inclusions for the entire volume of a strip such as a rolled metallic sheet, the following two techniques are proposed, having different arrangements of the ultrasonic probe (detecting head):

(1) A technique comprising testing a rolled metallic sheet while carrying the same, by arranging a plurality of ultrasonic probes in the width direction of the rolled metallic sheet to be tested, as disclosed in Japanese Unexamined Patent Publication No. 60-78345; and (2) A technique of testing a rolled metallic sheet while carrying the sheet by scanning the rolled metallic sheet in a direction substantially at right angles to the carrying direction of the sheet with ultrasonic probes, as described above, arranged in the width direction of the rolled metallic sheet.

Of these two types of immersion testing techniques, the technique (2) inevitably takes the form of a batch testing, and for the practical online application on a production line of a strip, the technique (1) is more suitable.

The immersion ultrasonic testing techniques are classified in terms of the kind of the ultrasonic probe into a pulse-who technique using a transmitting/receiving probe, a pulse-who technique using a double crystal ultrasonic probe, and a transmission technique based on arrangement of transmitting probe and receiving probe face to face with a strip to be tested between them.

In general, however, the ultrasonic beam is focused into a spot ("spot focused," for example, with a diameter of 1 mm) in these techniques for increasing the detectability of the flaws to a sufficient level. Consequently, in these techniques, a large number of probes are required corresponding to the testing area. Thus, the number of the parts for the detecting instrument is large, which increases cost. The pulse-echo technique has a disadvantage of the presence of a dead zone directly below the surface of the strip.

In view of the disadvantages of the above-mentioned techniques, the present inventors proposed a testing method as disclosed in Japanese Unexamined Patent Publication Nos. 7-253414 and Japanese Unexamined Patent Publication No. 11-083815, that solves the problems involved in the test using above-described spot focused ultrasonic probe requiring many probes for testing the full volume.

The proposed method comprises conducting the pulse-echo testing by configuring the flaw detecting heads (hereinafter referred to as "detecting heads") in an immersion and transmission-type arrangement. The term "transmission-type arrangement" means arranging a transmitting head and a receiving head face to face with the strip to be tested between them.

This method comprises transmitting a line-focused ultrasonic beam in the thickness direction of the strip, and receiving a echo from the flaw with a receiving head including a probe array of piezoelectric elements arranged in the width direction of the strip to be tested.

More specifically, the transmitting head comprises line-focused transmitting probe arrays arranged in the width direction of the strip to be tested, and the receiving head comprises line-focused receiving probe arrays arranged also in the width direction of the strip to be tested. The transmitting probe array and the receiving probe array are arranged face to face on the opposite side of the strip. Part of ultrasound transmitted with the transmitting probe arrays is reflect at the flaw and is received with the receiving probe arrays faced transmitting probe arrays (see FIGS. 3 and 4).

The method permits detection of flaws, if any, in the strip to be tested without a dead zone directly below the top surface and the bottom surface by using the configuration as described above. The detecting head having this configuration is hereinafter referred to as an "ultrasonic line sensor."

Functions of the ultrasonic line sensor are illustrated in FIG. 7(A), where:

T1: a wave that is transmitted from the transmitting probe array, and reaches the receiving probe array.

T2: a wave that is transmitted from the transmitting probe array, reflected at the back surface of the strip to be tested, reflected at the upper surface of the strip to be tested, and reaches the receiving probe array.

F1: a flaw echo that is part of ultrasound transmitted from the transmitting probe array, reflected at the upper surface of the flaw, reflected at the upper surface of the strip to be tested, and reaches the receiving probe array.

F2: a flaw echo that is part of ultrasound transmitted from the transmitting probe array, reflected at the back surface of the strip to be tested, reflected at the back surface of the flaw, and reaches the receiving probe array.

Flaw echoes F1 and F2 appearing between the transmission waves T1 and T2 are passed by a gating circuit, and when F1 or F2 has a amplitude more than a predetermined threshold voltage, it is detected as a flaw.

The line-focused probe array, having a wide range of testing in the width direction covered by a single detecting head, is preferable for the detection of flaws in a strip in transfer.

When detecting a flaw using immersion testing apparatus, the liquid (water) immersing technique is important for maintaining a satisfactory coupling between the ultrasonic probe and the steel sheet, i.e., for improving the detecting reliability. The applicable conventional techniques include the waterjet technique disclosed in Japanese Unexamined Patent Publication No. 7-113795, and the water tank immersion technique using a sealing pinch roll disclosed in Japanese Unexamined Patent Publication No. 5-149929, as well as the technique disclosed in Japanese Unexamined Patent Publication No. 60-78345.

However, because there are the following problems (1) to (3) for the application of the water jet technique disclosed in Japanese Unexamined Patent Publication No. 7-113795 to continuous testing over the entire volume of the strip, it is considered desirable to apply the immersion testing technique using a liquid tank.

(1) The necessity of arranging many probes in the width direction of the strip requires many nozzles for forming a water jet, many parts, and a more complicated apparatus. This requires a higher equipment cost and a complicated maintenance operation. The many nozzles increase the probability of occurrence of malfunctioning nozzles, and tend to cause a decrease in reliability of the apparatus.

(2) While it is conceivable to house a plurality of probes in a single nozzle, the increase in the size of the waterjet causes the force of the water to diffuse and exceed the surface tension of the waterjet, thus making it impossible to form a stable waterjet.

(3) Collision of water causes more serious fluctuations of the height of the carrying path of the rolled metallic sheet, irrespective of the number of probes, accordingly leading to deterioration of the detecting reliability. If the rolled metallic sheet is separated more from the nozzle to avoid this, it becomes impossible to form a water jet.

The water tank immersion technique using a sealing pinch roll disclosed in Japanese Unexamined Patent Publication No. 5-149929 has, on the other hand, an advantage of permitting testing without changing the height of the carrying path of the rolled metallic sheet. According to an investigation carried out by the present inventors, however, application of this technique to automatic ultrasonic testing of a rolled metallic sheet causes the following problems when the carrying speed of the sheet is higher and ultrasonic testing requires a higher sensitivity.

(1) Bubbles tend to easily go into the gap between the ultrasonic probes and the rolled metallic sheet. These bubbles generate a bubble echo as shown in FIG. 7(B), and this echo may be falsely interpreted as a flaw echo. The propagation of the flaw echo may be interrupted by the bubbles, thus it will be impossible to accomplish detection of the actual internal flaw. According to an investigation carried out by the present inventors, generation of bubbles is caused by entrainment of air by rotation of the upper sealing roll partially exposed on the water surface.

(2) Because of a large quantity of water outflow at the gap of rolls, it is necessary to feed a large amount of water into the water tank. Gaps corresponding to the thickness of the rolled metallic sheet are produced at the axial ends of the upper and lower pinch rolls (portions not in contact with the running rolled metallic sheet), and the amount of leakage water from these portion cannot be disregarded.

Japanese Unexamined Patent Publication No. 5-149929 and Japanese Unexamined Patent Publication No. 60-78345 disclose a method of immersing a rolled metallic sheet into water in a water tank by changing the carrying path of the rolled metallic sheet with deflector rolls.

However, a study conducted by the present inventors revealed that this method also has a problem of bubbles produced in water in the water tank as in the above-mentioned problem (1). According to a study carried out by the present inventors, a main source of bubble production is that, when the strip moves substantially vertically from the water upward, water adhering to the strip and coming up from the water surface, drops in a large quantity (a quantity almost exponentially proportional to the carrying speed of the strip) onto the water surface. Bubbles produced through this mechanism are entrapped into the water flow in the water tank, diffused throughout the entire tank, and cause the same problem as in (1) above.

It is conceivable that a large distance between the deflector rolls in the water tank and the water surface would correspond to a smaller possibility of producing bubbles by the water flow chiefly caused by these rolls. Naturally, however, this distance must be designed with a value larger than an anticipated one because there are no available guidelines for a specific value of the distance. Particularly, a design made based on the anticipation of high-speed would result in a deep water tank, and larger-scale equipment would be needed.

If the above problems are solved and it becomes possible to continuously test a carried strip by ultrasonic immersion testing technique, application of the technique to a manufacturing process of, for example, a steel sheet (steel strip) would be conceivable.

It is the conventional practice to perform continuous online testing of a cold-rolled steel sheet by the magnetic leakage flux testing technique on a production line after cold rolling, such as a finishing process. This testing is performed on a production line after cold rolling because determination of shipping can be made by testing carried out immediately before product shipment.

According to considerations made by the present inventors, however, the practice of testing on a production line after cold rolling has the following problems:

(1) Because the flow of manufacturing processes branches off after cold rolling in accordance with the plating method or the like, it is necessary to install a testing apparatus for each of the lines, leading to a higher cost.

(2) Even if a flaw is detected, possible uses of the cold-rolled sheet are limited after detection. When a flaw is discovered after finishing into a product size, for example, the destination of the sheet after testing cannot be changed. The defective sheet thus is rejected as a scrap, resulting in a large decrease in yield, leading to the economic disadvantage.

(3) Feeding back a factor causing the flaw requires much labor and time. That is, in order to feed back the factor, it is necessary to discover a process in which the flaw has occurred and the source of occurrence, and for this purpose, it is necessary to investigate shapes of flaws and relate the result with the operating conditions of each process. It is, however, difficult to clarify sources of flaws because many processes are present between the process in which the flaw has occurred and the process in which the flaw has been detected, and the sequence of works-in-process depends upon circumstances of treating timing on each line. Further, the investigation takes much time, so that a response (action) to avoid the occurrence of the flaw cannot be made in a sufficiently short amount of time.

(4) Information about the shape of flaw and the like is almost unavailable in the magnetic leakage flux technique. Discovery of a source therefore requires observation and investigation of the flaw, thus making the source discovering operation more complicated.

In the manufacture of a hot-rolled sheet, on the other hand, it is believed to suffice to provide quality assurance by testing through a sampling inspection of product hot-rolled steel sheets. The necessity or advantage of flaw investigation for the full width and full length as in cold-rolled steel sheets has never been established. Actually, testing apparatus permitting a high-accuracy, full width-full length testing at a high speed for hot-rolled steel sheets has not practically been provided until recently.

Even for hot-rolled steel sheets, however, there is an increasing demand from users for conducting operations of a working line or the like at a high efficiency without problems. It is therefore considered desirable to provide quality assurance based on total testing rather than only a probability assurance.

SUMMARY OF THE INVENTION

The present invention was made in view of the above-described problems and disadvantages, and provides continuous and high-reliability detection of flaws in a strip or the like being carried continuously. The present invention further can utilize a simple equipment configuration. The invention can provide a flaw detecting method and apparatus that permits detection regardless of high-speed transfer.

The invention provides a testing method and a manufacturing method of a steel sheet (steel strip), that permits easy preparation of counter-measures against flaws in the steel sheet and a rapid response to eliminate or reduce flaws in the steel sheet.

While an ultrasonic testing apparatus is generally used for detecting internal flaws, flaws to be tested (inspected) in the invention are not limited to internal flaws. That is, slivers, scabs, scale marks and gouges usually known as surface flaws, can be detected by the invention, so far as the flaws are exposed internal flaws, or contain internal flaws.

The invention can prevent the occurrence of a false indication resulting from the entanglement of bubbles and oversight of flaws, which are newly revealed problems in the continuous testing of a strip running in a liquid using an ultrasonic testing apparatus.

More specifically, an aspect of the present invention provides a method of detecting flaws in a strip, comprising, when continuously testing a strip carried continuously through a liquid by use of ultrasounds, inhibiting the generation of air bubbles in the liquid during carrying of the strip through the liquid.

The present invention also provides an apparatus for continuously testing for flaws in a continuously carried strip, comprising: a liquid; at least one carrying roll through which the strip is introduced to pass the strip through the liquid; and an ultrasonic testing apparatus that tests a portion of the strip that is immersed in the liquid. The apparatus further comprises a device that inhibits the generation of air bubbles in the liquid during carrying of the strip through the liquid.

In a more preferable exemplary embodiment of the first preferred embodiment, the device that prevents the liquid from dropping onto the liquid surface is a device that catches the liquid dropping in the direction of the liquid surface.

A first preferred embodiment of this aspect of the invention relates to a method of detecting flaws in a strip, comprising: carrying the strip at a speed within a range of from about 100 to about 1000 m/min; and testing the strip in the liquid while carrying the strip by at least one carrying roll in the liquid. In this testing, air bubble generation in the liquid is inhibited by (i) fully immersing each of at least one carrying roll into the liquid, and (ii) preventing the liquid that adheres to the strip and that is carried from the liquid to above the liquid surface from dropping back onto the liquid surface.

An exemplary embodiment of an apparatus for continuously testing for flaws in a continuously carried strip, comprises: a liquid; at least one carrying roll through which the strip is introduced to cause the strip to pass through the liquid; and an ultrasonic testing apparatus for testing a portion of the strip that is immersed in the liquid. Each of the at least one carrying roll that is in contact with the liquid is fully immersed in the liquid. The apparatus further comprises a device that prevents the liquid that adheres to the strip and that is carried from the liquid to above the liquid surface from dropping back onto the liquid surface.

In a more preferable exemplary embodiment of the first preferred embodiment, the device that prevents the liquid from dropping onto the liquid surface is a device that catches the liquid dropping in the direction of the liquid surface.

A second preferred embodiment of this aspect of the invention relates to a method of detecting flaws in a strip, comprising: carrying the strip at a speed within a range of from about 100 to about 1000 m/min; and testing the strip in the liquid while carrying the strip by at least one carrying roll in the liquid. In this testing, air bubble generation in the liquid is inhibited by (i) fully immersing each of the at least one carrying roll into the liquid, (ii) upon carrying the strip from the liquid to above the liquid surface, causing the moving direction of the strip to incline relative to a normal to the liquid surface, and (iii) preventing the liquid that adheres at least to the lower surface of the strip, and is carried from the liquid to above the liquid surface from dropping back onto the liquid surface.

An exemplary second preferred embodiment of an apparatus for continuously testing for flaws in a continuously carried strip, comprises: a liquid; at least one carrying roll through which the strip is introduced to pass the strip through the liquid; and an ultrasonic testing apparatus for testing a portion of the strip that is immersed in the liquid. Each of the at least one carrying roll that is in contact with the liquid is fully immersed in the liquid. The strip is guided by the carrying rolls so that the moving direction of the strip from the liquid to above the liquid surface inclines relative to the vertical direction. The apparatus also comprises a device that prevents the liquid that adheres to at least the back surface of the strip and that is carried from the liquid to above the liquid surface from dropping back onto the liquid surface.

A third preferred embodiment of this aspect of the invention relates to a method of detecting flaws in a strip, comprising: carrying the strip at a speed within a range of from about 100 to about 1000 m/min; and testing the strip in the liquid while carrying the strip by at least one carrying roll in the liquid. In this testing, air bubble generation in the liquid is inhibited by fully immersing each of the at least one carrying roll into the liquid such that the top of each carrying roll is immersed into the liquid to a depth of at least about 5 mm from the liquid surface.

A third preferred embodiment of an apparatus for continuously testing for flaws in a continuously carried strip, comprises: a liquid; at least one carrying roll through which the strip is introduced to pass the strip through the liquid; and an ultrasonic testing apparatus for testing the portion of the strip that is immersed in the liquid. In the apparatus, each of the at least one carrying roll in contact with the liquid is fully immersed in the liquid, and the vertical distance between the top of the fully immersed carrying roll and the liquid surface is at least about 5 mm.

A fourth preferred embodiment of this aspect of the invention relates to a method of detecting flaws to any one of the above-mentioned first to third preferred embodiments, comprising further inhibiting air bubble generation in the liquid by removing the liquid, that adheres to the strip and that is carried from the liquid to above the liquid surface, in the proximity of the liquid surface.

An exemplary apparatus according to a fourth preferred embodiment comprises a configuration according to any one of the above-mentioned first to third preferred embodiments, wherein there is provided near the liquid surface a device that removes the liquid that adheres to the strip and that is carried from the liquid to above the liquid surface.

In a particularly preferred exemplary embodiment of the fourth embodiment, the apparatus further comprises a device that catches the liquid that adheres to the strip and that is carried from the liquid to above the liquid surface to prevent this liquid from dropping back onto the liquid surface.

A fifth preferred embodiment of this aspect of the invention according to any one of the first to fourth preferred embodiments relates to a method of detecting flaws of a strip, comprising inhibiting air bubble generation in the liquid, upon carrying the strip from above the liquid surface into the liquid, by adjusting the moving direction of the strip so that the moving direction is substantially perpendicular to the liquid surface.

An exemplary apparatus according to a fifth preferred embodiment comprises a configuration according to any one of the first to fourth preferred embodiments and relates to an apparatus for detecting flaws of a strip. The strip is introduced into the liquid, by the carrying rolls so that the strip is substantially perpendicular to the liquid surface.

A sixth preferred embodiment of this aspect of the invention relates to a method of detecting flaws in a strip, comprising inhibiting the generation of air bubbles in the liquid by carrying the strip at a speed of less than about 200 m/min.

A second aspect of the invention relates to a method of detecting flaws of a strip according to the first aspect of the invention, wherein the strip is flattened prior to carrying the strip into the liquid.

An exemplary embodiment of an apparatus for detecting flaws of a strip according to the second aspect comprises an apparatus configuration of the first aspect of the invention, wherein there is provided a device that flattens the strip upstream of the liquid tank.

A third aspect of the invention relates to a method of detecting flaws in a strip according to the methods of the first or second aspect of the invention, wherein tension is applied to the strip in the moving direction of the strip during passage of the strip through the liquid.

An exemplary embodiment of an apparatus for detecting flaws of a strip according to the apparatus configuration of the first or second aspect of the invention comprises a device that applies tension to the strip in the moving direction of the strip in its passage through the liquid.

A fourth aspect of the invention relates to a method of detecting flaws in a strip according to any one of the first to third aspects of the invention, comprising, in the ultrasonic testing, arranging a transmitting probe and a receiving probe face to face in the thickness direction of the strip with the strip between them, transmitting a line-focused ultrasonic beam with a transmitting probe, and receiving an ultrasound reflected from an internal flaw in the strip with a receiving probe, thereby detecting the internal flaw in the strip.

An exemplary embodiment of an apparatus for detecting flaws in a strip comprises an apparatus according to the apparatus configuration of the first to third aspects of the invention, wherein the detecting heads of the ultrasonic testing are probe pairs for detecting flaws in a strip to be tested, by arranging transmitting probes and receiving probes face to face with the carried strip between them, transmitting line-focused ultrasonic beams with the transmitting probes, and receiving an ultrasound reflected from the flaw with the receiving probes. A plurality of the probe pairs are arranged in the width direction of the strip.

A fifth and additional aspect of the invention relate to a manufacturing method of a steel strip.

First, the fifth aspect of the invention relates to a method of detecting flaws in a steel strip according to any one of the first to fourth aspects of the invention.

A first preferred embodiment of the fifth aspect of the invention relates to a method of detecting flaws in a steel strip comprising carrying out the above-mentioned testing according to any one of the first to fourth aspects of the invention in the pickling process (equipment) for pickling a hot strip.

A first preferred embodiment of an apparatus comprises pickling equipment for pickling a hot strip, having an apparatus for detecting flaws in a strip according to any one of the first to fourth aspects of the invention.

A second preferred embodiment of the fifth aspect of the invention relates to a method of detecting flaws in a steel strip comprising carrying out the above-mentioned testing according to any one of the first to fourth aspects of the invention upstream of the cold rolling mill, or a cold rolling mill wherein there is provided an apparatus for detecting flaws in a strip at its entry side according to any one of the first to fourth aspects of the invention.

A sixth aspect of the invention relates to a method of manufacturing a cold-rolled steel sheet, comprising detecting a flaw in a steel strip, by use of a method according to any one of the first to fourth aspects of the invention, after hot rolling the strip and prior to cold rolling the strip.

An exemplary embodiment of an apparatus comprises equipment for manufacturing a cold-rolled steel sheet, including an apparatus for detecting flaws according to any one of the first to fourth aspects of the invention in the equipment, after a hot rolling mill prior to a cold rolling mill.

DETAILED DESCRIPTION OF PREFERRED EMBODIMENTS

Figure 1:
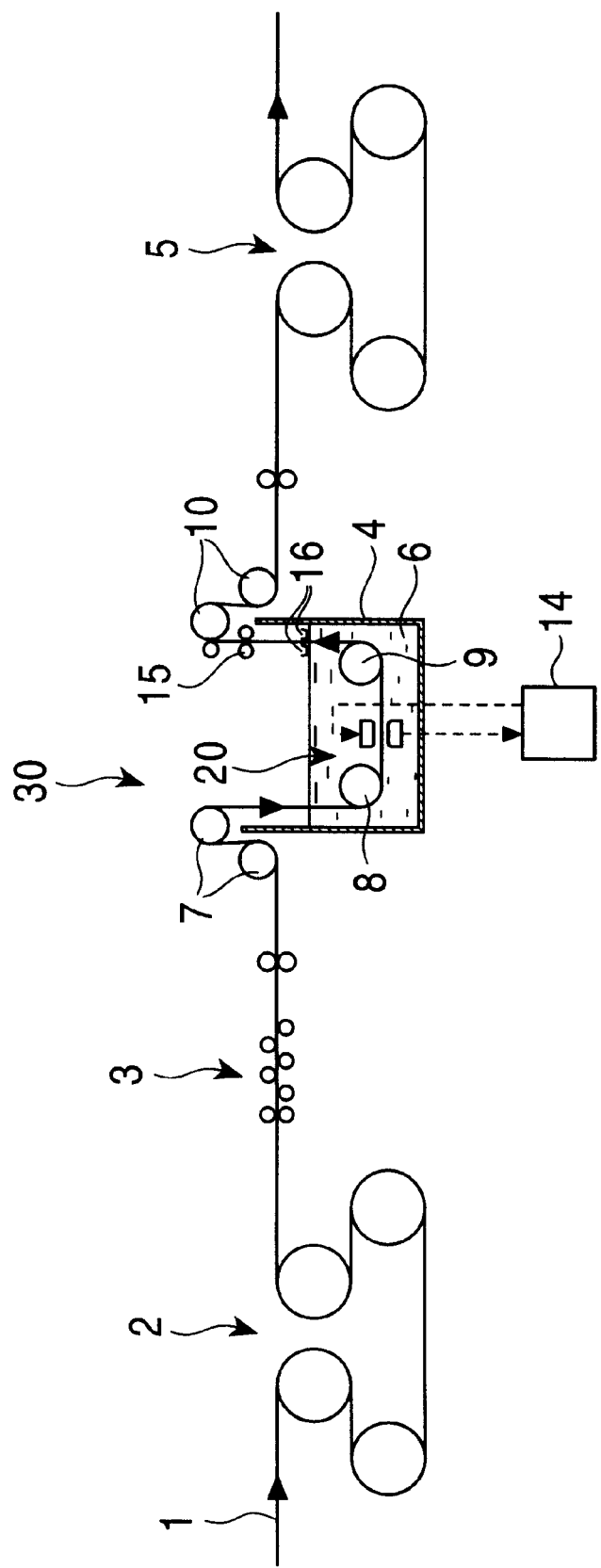
FIG. 1 illustrates an equipment configuration of the apparatus for detecting flaws in a strip of a first embodiment of the present invention.

The first aspect of the invention relates to a flaw detecting method for a strip. The method comprises, when continuously testing a strip carried continuously in a liquid by use of immersion ultrasonic testing technique, inhibiting air bubble generation in the liquid. The first aspect also relates to a flaw detecting apparatus in a strip for achieving this method.

A first preferred embodiment of the first aspect of the invention relates to a flaw detecting method for a strip. The method comprises carrying the strip at a speed within a range of from about 100 to about 1000 m/min; and testing the strip while carrying it by at least one carrying roll in the liquid. In this testing, the method comprises inhibiting air bubble generation in the liquid by (i) fully immersing each of the at least one carrying roll into the liquid; and (ii) preventing the liquid adhering to the strip carried from the liquid to above the liquid surface from dropping onto the liquid surface. The first preferred embodiment also provides a flaw detecting apparatus of a strip for achieving the method.

According to this embodiment, the liquid dropping from the portion of the strip above the liquid surface back toward the liquid surface such as the liquid adhering to the strip leaving the liquid surface, drops onto a device that shields the liquid, such as a device that catches the liquid. For example, the device can be a liquid reservoir. As a result, direct collision of the dropping liquid with the liquid surface is avoided, and the production of bubbles is reduced.

A second preferred embodiment of the first aspect of the invention relates to a flaw detecting method for a strip, comprising carrying the strip at a speed within a range of from about 100 to about 1000 m/min; and testing the strip while carrying it by at least one carrying roll in the liquid. In this testing, the method comprises inhibiting air bubble generation in the liquid by (i) fully immersing each part the at least one carrying roll into the liquid; (ii) upon carrying the strip from the liquid to above the liquid surface, causing the moving direction of the strip to incline relative to the perpendicular direction, and (iii) preventing the liquid adhering at least to the back surface of the strip carried from the liquid to above the liquid surface from dropping onto the liquid surface. The second preferred embodiment also provides a flaw detecting apparatus for a strip for achieving this method.

According to this embodiment, by inclining the strip relative to the vertical state, the liquid dropping from the upper surface of the strip flows obliquely on the strip upper surface and reaches the liquid surface. The impact force upon collision is thus alleviated as compared with the conventional art. As a result, the amount of air bubbles produced by the dropping liquid at least on the upper surface side is reduced. Even when a liquid removing device, such as liquid squeezing device, is provided on the strip upper surface side, the liquid dropping from the liquid removing device is received by the upper surface of the strip, and then reaches the liquid surface. Even in this case, therefore, the occurrence of air bubbles is inhibited because the liquid does not drop directly onto the liquid surface.

In this case, the inclination of the strip should preferably be at least 10° relative to the vertical direction.

When a liquid removing device is provided, the appropriate inclination angle varies with the location and size of the liquid removing device. The inclination angle should preferably be selected so that water dropping from the liquid removing device does not drop directly onto the liquid surface, but drops onto the upper surface of the strip (above the liquid surface).

The third preferred embodiment of the first aspect of the invention relates to a flaw detecting method for a strip, comprising carrying the strip at a speed within a range of from about 100 to about 1000 m/minute; and testing the strip while carrying it by at least one carrying roll in the liquid. In this testing, the method comprises inhibiting air bubbles brought about in the liquid by fully immersing top of each of the at least one carrying roll into the liquid so as to reach a depth of at least about 5 mm from the liquid surface. A third embodiment of a flaw detecting apparatus for achieving this method is also provided.

According to this embodiment, it is possible to regulate the distance between the fully immersed carrying roll and the liquid surface to a minimum value that is effective to prevent the entrainment of air bubbles. It is not therefore necessary to install the carrying rolls at an excessively deep position, so that it is not necessary to use a liquid tank having an excessively large scale.

The distance between the top of the fully immersed carrying roll and the liquid surface should preferably be at least about 5 mm for the following reasons. The carrying roll in the liquid rotates while trailing a liquid layer having a thickness corresponding to the rotational speed on the roll surface. When the top of the carrying roll is on the liquid surface or directly below the liquid surface, the liquid adhering to the roll surface goes up to a position higher than the liquid surface, and then drops from this position onto the liquid surface. Air bubbles are produced at the time of this dropping, and this causes the entrainment of air bubbles by the carrying roll. Production and entrainment of air bubbles by the carrying roll can therefore be prevented by preventing the liquid layer trailed by the surface of the rotating roll from going up to a position higher than the liquid surface. The thickness of the liquid layer trailed by the rotating roll surface varies with the roll diameter and the roll rotational speed. Particularly, the thickness is large as the roll diameter is larger, or as the rotational speed is higher. Within a practical range of roll diameter (of from about 300 to about 1,500 mm), this thickness was confirmed to be up to about 5 mm when the carrying speed of the strip was up to about 1,000 m/min. The distance between the top of carrying roll and the liquid surface can be at least about 5 mm.

When considering fluctuations of the liquid level during actual operation, the distance between the top of carrying roll and the liquid surface should preferably be at least 50 mm.

The fourth preferred embodiment of this aspect of the invention relates to a flaw detecting method according to any one of the first to third preferred embodiments, and comprising further inhibiting the generation of air bubbles in the liquid by providing a liquid removing device that removes the liquid adhering to the strip carried from the liquid to above the liquid surface, such as a liquid squeezing device like wringer rolls, in the proximity to the liquid surface. The fourth preferred embodiment also provides a flaw detecting apparatus for a strip for performing this method.

According to this embodiment, the drop path length of the liquid becomes shorter by removing the liquid adhering to the strip at a position near the liquid surface. As a result, any liquid dropping onto the liquid surface produces only a slight impact force, thus reducing the production of air bubbles.

The liquid removing device is provided at a position near the liquid surface as described above. The preferred position depends upon the carrying speed, physical properties of the liquid and other factors. It is desirable, however, to install the liquid removing device at a distance of from about 30 to about 600 mm from the water surface.

The fifth preferred embodiment of this first aspect of the invention relates to a flaw detecting method for a strip according to any one of the first to fourth preferred embodiments, and comprising inhibiting the generation of air bubbles in the liquid, upon carrying the strip from above the liquid level into the liquid, by adjusting the moving direction so that it is substantially perpendicular, to the liquid surface. The fifth preferred embodiment also provides a flaw detecting apparatus for performing this method.

According to this embodiment, it is possible to reduce the risk of entrainment of air bubbles upon immersing the strip into the liquid by adjusting the moving direction so that it is preferably perpendicular, or substantially perpendicular, to the liquid surface.

To be or substantially perpendicular to the liquid surface means an angle of about 90°±15° to the liquid surface. Within the range of up to 90°±45°, entrainment of air bubbles is relatively less frequent, leading however to the necessity of providing large-scale equipment.

The sixth preferred embodiment of the first aspect of the invention relates to a flaw detecting method for a strip, comprising inhibiting air bubbles brought about in the liquid by carrying the strip at a speed of less than about 200 m/min.

A second aspect of the invention relates to a flaw detecting method for a strip according to the first aspect of the invention, wherein the shape of the strip is flattened prior to carrying the strip into the liquid. The second aspect also provides a flaw detecting apparatus for a strip for performing this method.

According to the second aspect of the invention, even upon occurrence of a camber, an edge elongation or a body elongation in the strip, the detecting reliability is improved over the entire volume by flattening the strip shape prior to detection by use of the ultrasonic testing apparatus. A flat shape stabilizes the distance from the ultrasonic probe to the strip. With a view to improving the flatness of the strip shape, it is possible to improve the detectability by setting the position of the probe closer to the strip.

When simultaneously using the second aspect of the invention and the liquid removing device of the fourth preferred embodiment of the first aspect of the invention, it is possible to prevent a decrease in the liquid removing efficiency caused by a defective shape such as a camber of the strip, thus improving the bubble inhibiting effect by the liquid removing device.

Further, in the case of a hot strip, there is available a favorable effect of a lower risk of bringing foreign materials into the liquid tank for testing or accumulation of such foreign materials in the liquid tank. Brittle scale and adhesive materials on the outermost surface are previously removed by a flattening device such as a tension leveler.

In the second aspect of the invention, the flatness after flattening should preferably be the highest possible, and the flatness reachable by a usual leveler is sufficiently effective.

A third aspect of the invention relates to a flaw detecting method for a strip according to the method of the first or second aspects of the invention, wherein a tension is applied in the moving direction of the strip during its passage through the liquid. The third aspect also provides a flaw detecting apparatus for performing this method.

According to the third aspect of the invention, a tension is applied in the moving direction, thereby permitting testing with an ultrasonic testing apparatus in a flat state of the strip.

Because fluctuations of the pass-line are minimal, the detecting reliability is further improved. And further, in carrying the strip, it zigzags in the width direction, and this movement is also inhibited by applying the tension.

When using a tension leveler as a flattening device in the second aspect of the invention, and applying the third aspect of the invention, an improvement of an effect of flattening a defective shape such as a camber of the strip by tension can be achieved, thereby further improving the bubble inhibiting effect by the liquid removing device.

The fourth aspect of the invention relates to a flaw detecting method for a strip according to any one of the first to third aspects of the invention, and comprising, in ultrasonic testing, arranging a transmitting probe and a receiving probe face to face in the thickness direction of the strip with the strip between them, transmitting a line-focused ultrasonic beam with a transmitting probe, and receiving an ultrasound reflected at an internal flaw in the strip with a receiving probe, thereby detecting flaws in the strip. The fourth aspect also provides a flaw detecting apparatus for a strip for performing this method.

According to the fourth aspect of the invention, in which the area that can be tested by a detecting head is wide in the width direction, it is possible to detect the entire volume of the strip with less detecting heads (probes), thus permitting reduction of the number of parts in the apparatus.

An applicable detecting head is disclosed in Japanese Unexamined Patent Publication No. 7-253414.

Any equipment that includes transfer of the strip may be applied at any location for the method and the equipment of the first to fourth aspects of the invention. R is, however, desirable to select the most suitable embodiment based on the type of the strip to be tested and the kind of production line.

For a manufacturing process of a steel strip, for example, it is suitable to apply the fifth or sixth aspect of the invention.

The fifth aspect of the invention relates to a manufacturing method of a steel strip.

The first preferred embodiment of the fifth aspect of the invention relates to a flaw detecting method for a steel strip, comprising, in equipment including a pickling equipment for a hot-rolled strip after hot rolling, carrying out the above-mentioned testing according to any one of the first to fourth aspects of the invention. The first preferred embodiment also provides pickling equipment of a hot strip having a flaw detecting apparatus for a strip according to any one of the first to fourth aspects of the invention.

The second preferred embodiment of the fifth aspect of the invention relates to a flaw detecting method for a steel strip, comprising carrying out the testing according to any one of the first to fourth aspects of the invention upstream of the cold rolling mill, or a cold rolling mill provided with the flaw detecting apparatus for a strip upstream according to any one of the first to fourth aspects of the invention.

The sixth aspect of the invention relates to a manufacturing method of a cold-rolled steel sheet, comprising detecting a flaw in a steel strip by a method according to any one of the first to fourth aspects of the invention, after hot rolling the strip and prior to cold rolling the strip. The sixth aspect also provides a flaw detecting apparatus for a strip for performing this method.

When a steel strip is to be tested, flaws detectable by the present invention include: (a) internal flaws, such as inclusions, voids; (b) surface flaws caused by inclusions such as a sliver, (c) surface flaws caused by hot rolling such as a scab, and the hike; (d) surface flaws caused by entanglement of oxides such as a scale mark; and (e) surface flaws caused by contact of the strip with mechanical equipment such as a gouge.

All of these flaws are detectable by the method of the invention, but testing may be applied to specific flaws.

By using the fifth aspect (particularly the first and second preferred embodiments) and the sixth aspect of the invention, most of internal flaws and surface flaws can be detected by a testing concentrated at a location.

There is usually a pickling process of a hot strip between the hot rolling process and the cold rolling process. The testing apparatus is most suitably installed in the pickling process. A main reason for this is that the carrying speed of the steel strip in the pickling process is lower than in the hot rolling or cold rolling process, and there is available a relatively large permissibility of the carrying speed.

In the invention, it is easy to investigate a source of flaws and an early response can be made because flaws are detected between the completion of hot rolling and the start of cold rolling. Flaw testing is conducted immediately after the processes forming flaws, i.e., the steel making and hot rolling processes.

The cold-rolled steel sheet after cold rolling is processed in an appropriate production line and under appropriate conditions corresponding to the use. By carrying out flaw testing before cold rolling, flaw information is available prior to branching off of the production line. It is therefore possible to change the use of steel and select downstream process conditions or a production line on the basis of the testing information.

For the reasons described above, the following practice should preferably be used in order to manufacture a steel sheet (steel strip) by applying the fifth or the sixth aspect of the invention to flaw testing.

When manufacturing a hot-rolled steel sheet, it is also desirable to conduct testing after hot rolling, and modify the process conditions for the processes upstream of the testing position, on the basis of the testing information.

When manufacturing a cold-rolled steel sheet, it is also desirable to carry out testing after hot rolling and before cold rolling, and modify the process condition for the processes upstream of the testing position on the basis of the testing information.

When manufacturing a cold-rolled steel sheet, it is desirable to carry out testing after hot rolling and before cold rolling, and modify or select process conditions for the processes downstream of the testing position, or select a production line for the steel sheet after cold rolling. In some cases, it suffices to remove the portion containing the flaw.

The first embodiment of the first aspect of the invention will now be described with reference to the drawings.

FIG. 1 is a schematic view illustrating an equipment configuration of the flaw detecting apparatus of this embodiment. The steel strip 1 is carried from the left (upstream side) to the right (downstream side) in FIG. 1. As shown in FIG. 1, from the upstream side toward the downstream side, the equipment includes an upstream-side bridle roll 2, a tension leveler 3, a liquid tank 4, and a downstream-side bridle roll 5. The tension leveler 3 corrects the steel strip flatness (i.e., flattens the steel strip). The upstream-side bridle roll 2 and the downstream-side bridle roll 5 apply tension to the steel strip.

Figure 2:
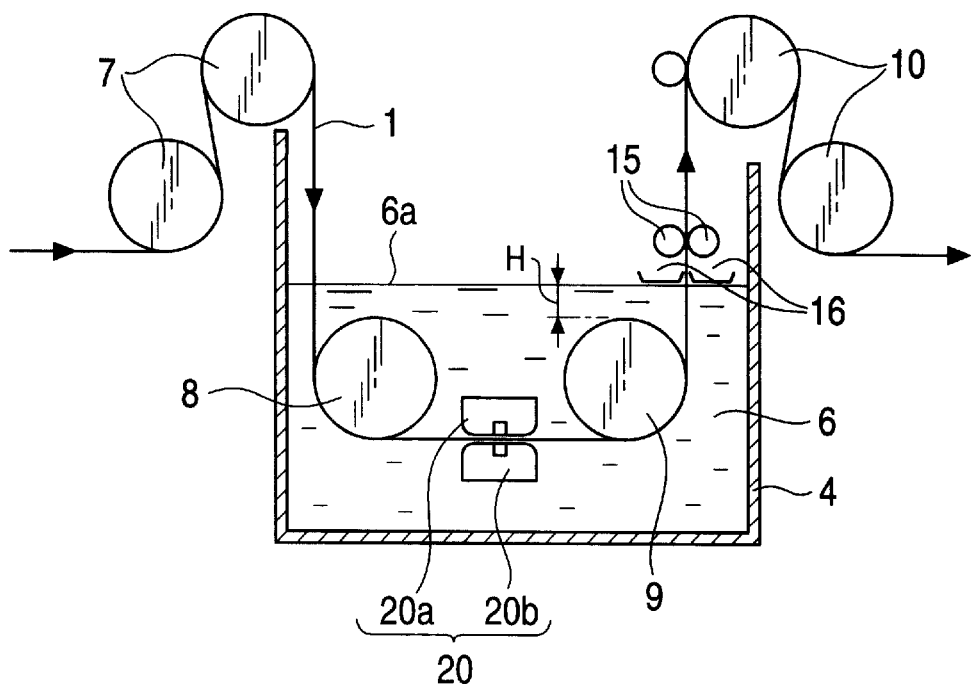
FIG. 2 illustrates a configuration of a liquid tank and its surroundings of the first embodiment of the invention.

FIG. 2 illustrates a configuration of the liquid tank and surroundings of this embodiment, comprising a liquid 6 contained in the liquid tank 4 (water in this embodiment); a pair of first carrying rolls 7 located above the water surface 6a; a second carrying roll 8 filly immersed in the water 6; a third carrying roll fully immersed in the water 6; and a pair of fourth carrying rolls 10 located above the water surface 6a.

The carrying path of the steel strip 1 is changed to vertically downward and introduced into the water 6 in the liquid tank 4 by the first carrying roll 7 arranged upstream of the liquid tank 4 and the second carrying roll 8 in the water 6. The carrying direction of the steel strip 1 is then changed to horizontal by the second and third carrying rolls 8 and 9. Then, the carrying direction is changed to vertical by the third carrying roll 9 and the fourth carrying roll 10, and the steel strip 1 leaves the water 6 (i.e., leaves the liquid tank 4). Thereafter, the steel strip 1 is guided by the fourth carrying roll 10 toward the downstream-side bridle roll 5.

Each of respective first and fourth carrying rolls 7 and 10 comprises two rolls because the carrying path of the steel strip 1 is low in height in the example shown in FIG. 2. More specifically, if the steel strip 1 is guided by a single roll directly into the liquid tank 4, a sufficient depth of the liquid tank 4 cannot be ensured in this case. The carrying path of the steel strip 1 is therefore once raised so as to permit introduction into the liquid tank 4. When a sufficient space is available, therefore, it is not necessary that each of these carrying rolls include two rolls.

Figure 3:
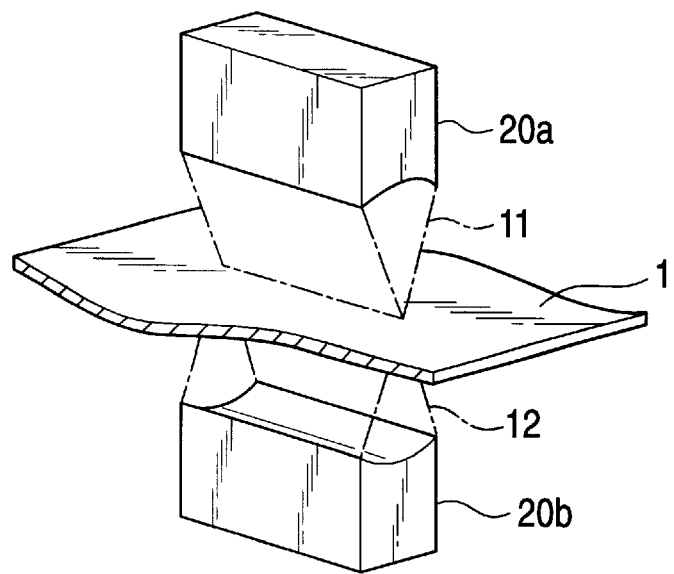
FIG. 3 illustrates a configuration of probes of the ultrasonic testing apparatus, which are detecting heads of an embodiment of the invention.

Probes 20 of an ultrasonic testing apparatus serving as detecting heads for the ultrasonic testing apparatus are arranged between the second carrying roll 8 and the third carrying roll 9. A conceptual view of the probes 20 of the ultrasonic testing apparatus is illustrated in FIG. 3. A transmitting probe 20a and a receiving probe 20b are respectively linear probe arrays and arranged face to face in the thickness direction of the steel strip 1 with the steel strip 1 between them. In FIG. 3, a line-focused beam 11, and a receiving beam 12 are shown.

Figure 4:
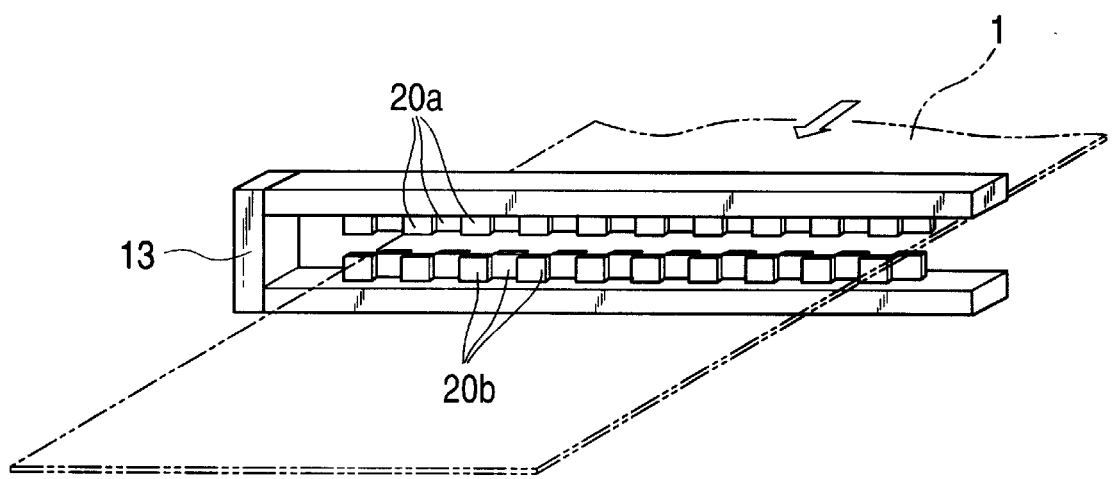
FIG. 4 illustrates an arrangement of probes of the ultrasonic testing apparatus of an embodiment of the invention.

A plurality of probes 20 of the ultrasonic testing apparatus having the configuration as described above are arranged in the width direction of the steel strip 1 as shown in FIG. 4. That is, the arranged transmitting probes 20a and receiving probes 20b are supported by a U-shaped frame 13. The transmitting probes 20a and the receiving probes 20b are arranged to form zigzag shapes, to eliminate a gap of the detection area while avoiding interference of space between adjacent probes. This arrangement permits testing of the entire volume of the steel strip. The receiving probes 20b may be arranged above the strip and the transmitting probes 20a may be arranged below it. Also, transmitting and receiving probes may be alternately arranged in a sequence (for example, transmitting probe—receiving probe—transmitting probe . . . in the width direction for the upper side, and receiving probe—transmitting probe—receiving probe . . . for the lower side).

Figure 7A:
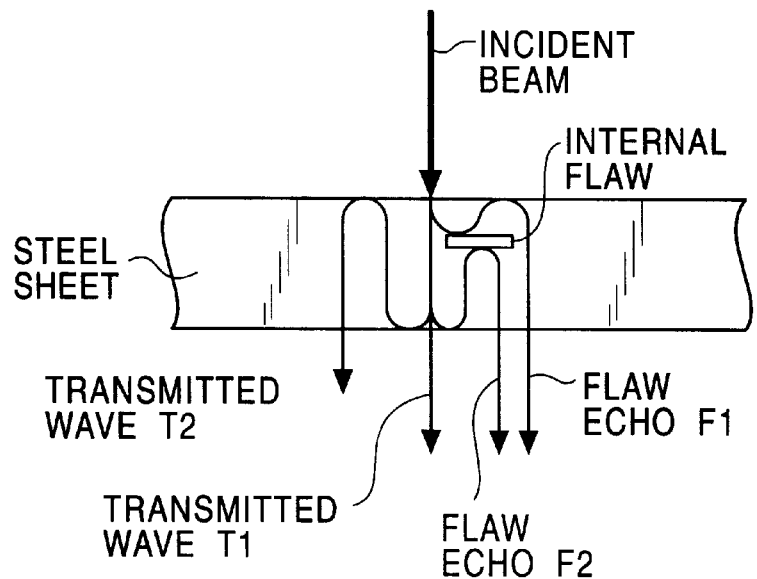
FIG. 7(A) illustrates a transmission wave and a flaw echo in ultrasonic testing of a strip using an ultrasonic line sensor.
Figure 7B:
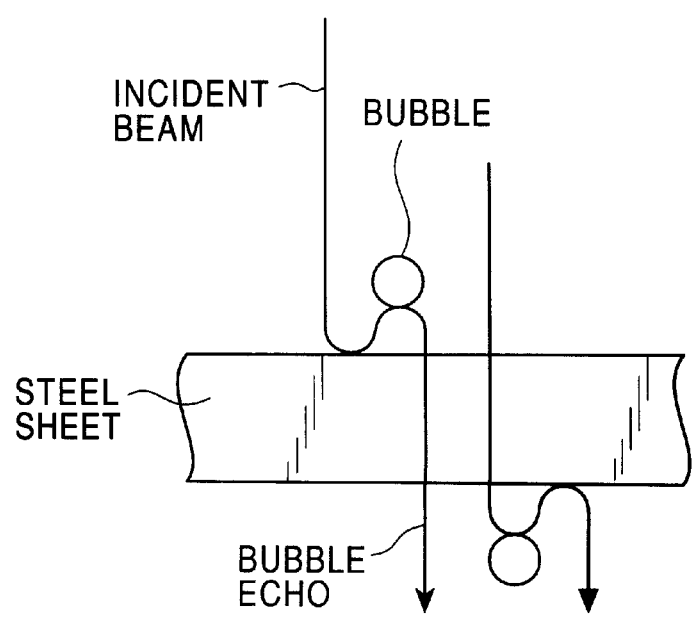
FIG. 7(B) illustrates bubble echoes in ultrasonic testing of a strip using an ultrasonic line sensor.

All of the probes 20 are connected to the testing apparatus main body 14. In the testing apparatus 14, flaw echoes F1 and F2 appearing between transmission waves T1 and T2 are passed by a gating circuit in accordance with the principle shown in FIG. 7. When the amplitude of the flaw echo exceeds a predetermined threshold voltage, it is detected as a flaw. The information of the detected flaw is supplied to the upstream and downstream processes.

Between the third carrying roll 9 and the fourth carrying roll 10, a wringer roll 15 serving as a liquid removing device (in this embodiment, a liquid squeezing device) is arranged at a position near the water surface 6a. Further, between the wringer roll 15 and the water surface 6a, a liquid reservoir 16 as a liquid shielding device, (is this embodiment, a liquid catching device) is arranged. The liquid reservoir 16 catches the liquid dropping directly along the steel strip 1 from the steel strip 1, or dropping along the liquid removing device. The liquid reservoir 16 can be located above the water surface 6a, or can be in contact with water 6 in the liquid tank 4. Water received in the liquid reservoir 16 may be returned back to the liquid tank 4 by, for example, allowing it to overflow to the surroundings, or may be discharged out of the liquid tank 4. While FIG. 2 shows a container-type liquid reservoir 16, it can alternatively be a flat member such as a shielding plate. The liquid reservoir 16 should preferably be near the steel strip (up to 10 mm). However, when the rate of liquid dropping along the liquid removing device is high, the liquid reservoir suffices to be at a position permitting receiving the liquid dropping along the liquid squeezing device, and it is not always necessary that it is near the steel strip. A material that does not damage the steel strip, such as rubber, can be attached to the liquid reservoir and the steel strip can be brought into contact with this material.

A vacuum sucking nozzle arranged near the surface of the steel strip to serve as a shielding device in place of the liquid reservoir is also effective for sucking and excluding the liquid dropping along the steel strip.

In the flaw detecting apparatus having the configuration as described above, the steel strip 1 is carried while being subjected to tension in a direction along the carrying direction, i.e., in the longitudinal direction by the upstream-side bridle roll 2 and the downstream-side bridle roll 5. Before transfer to the liquid tank 4, the steel strip 1 is continuously flattened by the tension leveler 3. Then, the steel strip 1 enters into the water 6 by being guided by the respective first and second carrying rolls 7 and 8. At this point, the generation of air bubbles is minimized during immersion of the steel strip 1 into the water 6 by immersing the steel strip 1 vertically into water 6.

Further, the steel strip 1 moves horizontally in the water 6 under the effect of the second and third carrying rolls 8 and 9. During this movement, the ultrasonic testing apparatus comprising the probes 20 and the testing apparatus main body 14 performs testing of flaws.

Thereafter, the steel strip 1 moves vertically upward along the third and fourth carrying rolls 9 and 10, and leaves the water surface 6a. At this point, water 6 adhering to the steel strip 1 is squeezed by the wringer roll 15 serving as a liquid squeezing device near the water surface 6a, and drops from the installation height of the wringer roll 15, and is received by the liquid reservoir 16 serving as shielding device. This prevents direct collision of the dropping liquid with the water surface 6a, and generation of air bubbles caused by the liquid dropping from the steel strip 1 portion above the water surface 6a is prevented.

Because the dropping liquid is received by the liquid reservoir 16, it is not always necessary to provide the liquid removing device such as the wringer roll 15. However, the bubble preventing effect is further improved by the liquid removing device. By reducing the dropping path length of the liquid by the liquid removing device, rebound of the liquid after having hit the liquid reservoir 16 is reduced. The liquid removing device also prevents water 6 from being carried to the downstream processes, together with the steel strip 1.

In the flaw detecting apparatus of this embodiment (first embodiment), ultrasonic line sensors serve as detecting heads of the ultrasonic testing apparatus. Testing is therefore free from a dead zone, with satisfactory detection reliability. A smaller number of detection heads (probes) suffices even when the entire volume of the steel strip 1 is to be tested.

In the flaw detecting apparatus of this embodiment, production of air bubbles upon the steel strip 1 entering into the water 6 and production of air bubbles during movement of the strip upward from the water surface 6a are inhibited to the minimum. A false detection and disturbance of ultrasound propagation caused by bubbles are prevented, thus improving the detection reliability. Because the carrying rolls 8 and 9 in contact with water are fully immersed in the water 6, it is possible to prevent entrainment of air bubbles by the rotation of the carrying rolls 8 and 9.

In the flaw detection apparatus of this embodiment, furthermore, flatness of the steel strip 1 is corrected prior to testing, and testing is carried out in a state in which the strip is subjected to tension. As a result of this correction and tension, the steel strip 1 becomes more flat, and this permits flaw detection of the steel strip 1 at a higher reliability. A higher flatness of the steel strip 1 also leads to an improvement of the effect of liquid squeezing by the wringer roll 15, resulting in an improvement of inhibiting effect of the bubble generation.

While the aforementioned embodiment has been described for a case where the wringer roll 15 serves as a liquid removing device, any other suitable liquid removing device such as a wiper may also be used.

When the strip shape is originally flat, it is not necessary to provide a flattening device, such as a tension leveler 3, or a tension applying device, such as the bridle rolls 2 and 5. For preventing zigzag running, it is desirable to apply tension by a bridle roll or the like. The flattening device is not limited to the tension leveler 3, and a temper rolling mill or a roller leveler may also be used. The bridle roll may be replaced by any other suitable device that functions as a tension applying device. When using a bridle roll, it is not limited to the four-roll type one as shown. For example, a two-roll or three-roll bridle roll may also be employed.

While water 6 is shown as a liquid in the liquid tank 4, any other suitable liquid may be used in accordance with properties of the strip to be tested.

The first embodiment has been described with the two carrying rolls 8 and 9 fully immersed in the water 6. However, only one carrying roll may alternatively be fully immersed. More specifically, in this embodiment, a horizontal carrying path is provided in the water 6 for testing the steel strip 1. However, the probes 20 of the ultrasonic testing apparatus may alternatively be arranged on a non-horizontal carrying path. However, measurement at a position spaced apart from the liquid surface 6a permits reduction of any disturbance of air bubbles. In embodiments, three or more carrying rolls can be provided in the water 6.

The second embodiment of the invention will now be described with reference to FIG. 5. Component parts identical with, or similar to, those in the aforementioned first embodiment have the same reference numerals, and detailed description thereof will be omitted.

Figure 5:
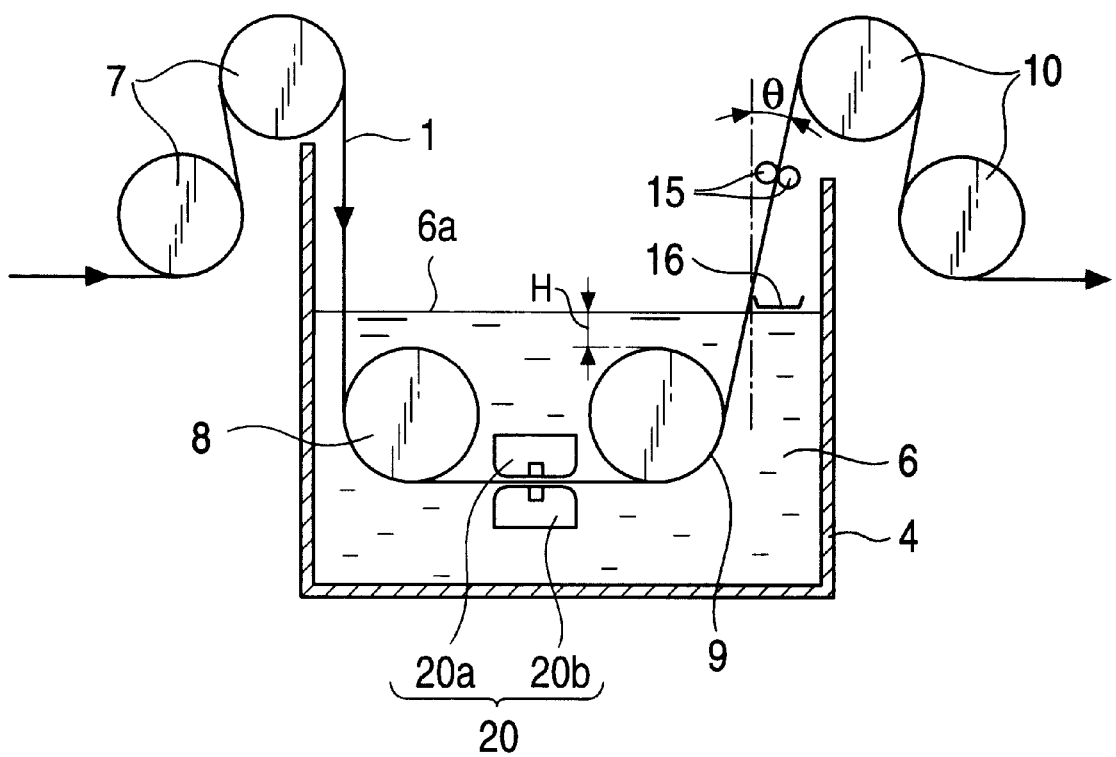
FIG. 5 illustrates a configuration of a liquid tank and its surroundings of a second embodiment of the invention.

This second embodiment has the same basic configuration as that of the first embodiment, except that, in this embodiment, as shown in FIG. 5, the relative positions of the third carrying roll 9 and the fourth carrying roll 10 are changed such that the carrying path of the steel strip 1 leaving the water surface 6a is inclined by a prescribed angle θ from the perpendicular direction (vertical direction to the water surface 6a). The liquid reservoir 16 if provided only on the back surface side of the steel strip 1.

Inclination of the carrying path of the steel strip 1 leaving the water surface 6a causes water 6 adhering to the upper surface of the steel strip 1 to drop obliquely along the steel strip 1. As a result, the hitting force with the water surface 6a is reduced on the upper surface side of the steel strip 1, thus reducing production of air bubbles. Even by omitting the liquid reservoir 16 on the upper surface of the strip, therefore, the bubble production reducing effect is still available, and advantages similar to those of the first embodiment are obtained.

In this embodiment, a wringer roll 15 serving as a liquid squeezing device is provided near the water surface 6a to further reduce production of air bubbles.

In this embodiment also, the top of the second and third carrying rolls 8 and 9 are spaced apart from the water surface by a distance H of at least 5 mm. As a result, even when the steel strip 1 is carried at 400 m/min, the generation of air bubbles is largely reduced.

Application of the invention to a steel strip manufacturing process will now be described. First, a first form of application will be described with reference to FIG. 9. This form of application relates to manufacturing equipment of a cold-rolled steel sheet. The equipment has a configuration of, from the upstream side, blast furnace—converter—(degassing equipment)—continuous casting equipment—(slab storage)—hot rolling—pickling process of hot-rolled steel sheet—cold rolling process—continuous annealing process—(secondary cold rolling or box annealing process)—temper rolling process—finishing process. The production line subsequent to cold rolling (continuous annealing process—temper rolling process—finishing process) is branched into a different production line corresponding to the final product. The above-mentioned production line subsequent to the cold rolling process is only an example, and depending upon the kind of steel, it may contain a process other than the above such as a plating process.

Figure 9:
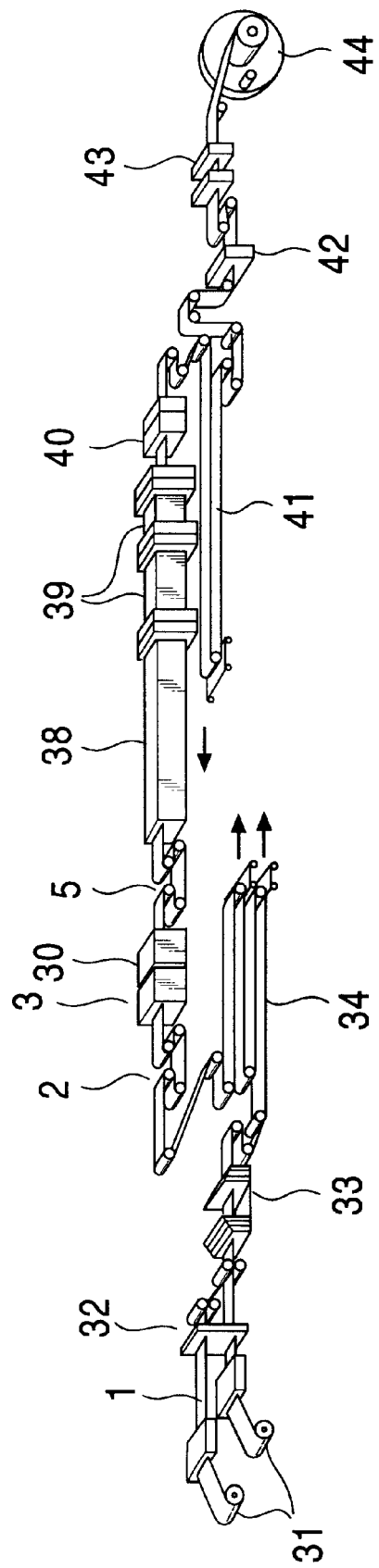
FIG. 9 illustrates equipment for a pickling process in an embodiment utilizing the invention.

Typical pickling equipment that pickles a hot-rolled steel strip is illustrated in FIG. 9. In this pickling equipment, from the upstream side, a payoff reel 31, a shear 32, a welding machine 33, an entry-side looper 34, an entry-side bridle roll 2, a tension leveler 3, an exit-side bridle roll 5, a pickling tank 38, a rinsing tank 39, a drier 40, an exit-side looper 41, a trimmer 42, a shear 43, and a coiler 44, are arranged in this order. The hot-rolled steel sheet is uncoiled from the payoff reel 31 and subjected to the pickling.

In this arrangement, an ultrasonic testing apparatus 30 as shown in FIG. 1 is arranged between the tension leveler 3 and the exit-side bridle roll 5 located on the entry side of the pickling tank 38.

At this point, the tension leveler 3 produces cracks in scale on the surface of the steel strip (hot-rolled steel sheet) 1 to accelerate pickling in the pickling tank 38, also has a function of flattening the sheet before testing, and serving as a flattening device for testing. The bridle rolls 2 and 5 arranged before and after the testing apparatus 30 apply a longitudinal tension to the material to be tested. The tension leveler 3 and the bridle rolls 2 and 5 form a part of the testing equipment (flaw testing apparatus) together with the ultrasonic testing apparatus 30.

The testing equipment has the same configuration as that in the first embodiment, as shown in FIGS. 1 and 2. An anti-rust additive or the like for preventing rust of the steel strip (hot-rolled steel sheet) 1 is added to the water 6 in the liquid tank 4.

The testing apparatus main body 14 detects flaws in the same manner as in the first embodiment. Information about the detected flaw is fed, for example, to the operating and control sections of the upstream or downstream processes.

In the manufacturing equipment of a cold-rolled steel sheet as described above, the steel strip (hot-rolled steel sheet) 1 is continuously tested (flaw tested) while being carried prior to pickling. That is, the steel strip (hot-rolled steel sheet) 1 after hot rolling and before pickling is carried in a state in which it is subjected to a longitudinal tension by the upstream-side bridle roll 2 and the downstream-side bridle roll 5, and continuously flattened by the tension leveler 3. Then, the steel strip 1 is immersed into water in the liquid tank 4 by the carrying rolls 7 to 10, moves horizontally in water, and carried outside the liquid tank 4. The steel strip 1 is continuously tested by the ultrasonic line sensor 20 of the ultrasonic testing apparatus 30 during horizontal displacement in water.

In this first arrangement (first form of application), the pickling process is located between the completion of hot rolling and the start of cold rolling, so that almost all flaws to be detected can be detected through testing at a single location in the pickling process.

In this arrangement, deterioration of the detecting reliability caused by air bubbles can be prevented. That is, the steel strip (hot-rolled steel sheet) is vertically introduced to the liquid surface; a liquid reservoir is provided on the exit side; and a wringer roll is provided near the water surface.

The carrying roll in contact with water is fully immersed into water.

By adopting the above-mentioned testing equipment, it is possible to conduct continuous testing over the entire volume even at a carrying speed of from about 100 to about 1000 m/min, or preferably, during high-speed passage of the strip of the order of about 300 to about 1,000 m/min. Because the passing speed through the pickling equipment should preferably be within a range of from about 100 to about 1000 m/min, the pickling equipment is suitable for installation of the flaw detecting apparatus. In a common pickling equipment, a suitable speed for pickling is about 400 m/minute.

As suggested by this arrangement, the following are advantages of testing on the entry side of the pickling tank 38: (a) Usually, the steel strip immersed in water for testing should be rinsed and dried. Before the pickling tank, however, this is not necessary. As parts of the pickling process, the strip having left the pickling tank is rinsed and dried in a rinsing tank 39 and a drier 40. (b) A tension leveler can be arranged on the entry side of the pickling tank for improving the pickling effect. It is not, therefore, necessary to provide a flattening device separately for testing. (c) In the pickling process, the portions in the vicinity of the pickling tank show the most stable carrying speed. This is because control of the pickling time is important for this process.

The equipment of this form of arrangement (first arrangement) is manufacturing equipment of a cold-rolled steel sheet. However, even when a hot-rolled steel sheet before cold rolling is shipped as an intermediate product, this is applicable for quality control. It is not, therefore, necessary to separately provide flaw testing equipment for hot-rolled steel sheet.

Figure 8:
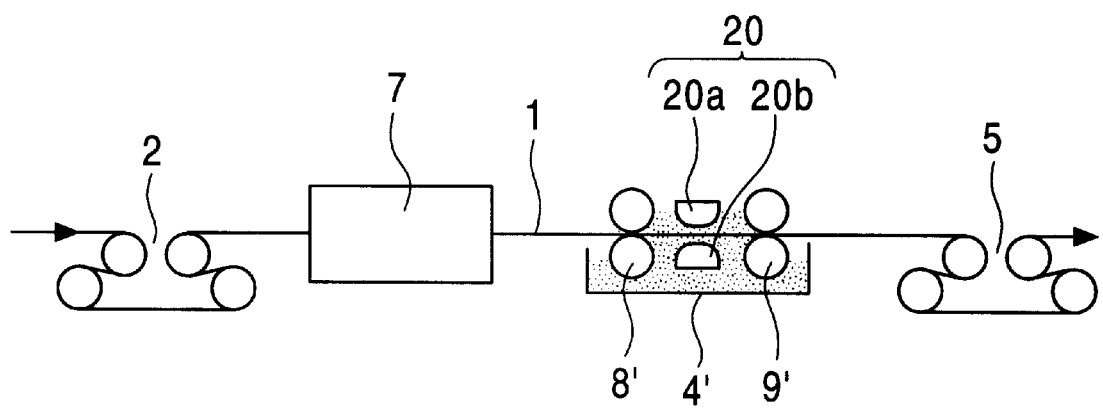
FIG. 8 illustrates an exemplary immersion technique for testing.

In the above-mentioned first arrangement, the immersion method using a water tank containing rolls fully immersed is used. However, the present invention is not limited to such a testing method. For example, a different water immersion technique as shown in FIG. 8 may be used. In the example shown in FIG. 8, there are used two pairs of rolls 8' and 9' sealing water (liquid) while carrying the steel strip. In the case of the immersion technique shown in FIG. 8, air bubbles should preferably be prevented from coming in by using a low carrying speed of the steel strip of less than about 200 m/min.

An ultrasonic testing apparatus based on the known ultrasonic testing technique using focused probe may be adopted in place of the ultrasonic line sensor 20. However, this leads to more probes (detecting heads), and this may result in a more complicated equipment configuration and a decrease in the detecting reliability.

While the above-mentioned embodiment has been described as to an arrangement in which a testing equipment is provided in the pickling process, the testing equipment can alternatively be installed at a different position, as far as the position is between the hot rolling line and the cold rolling line of the strip. Other positions include, for example, entry side equipment of cold rolling mill including the trimmer.

Figure 10:
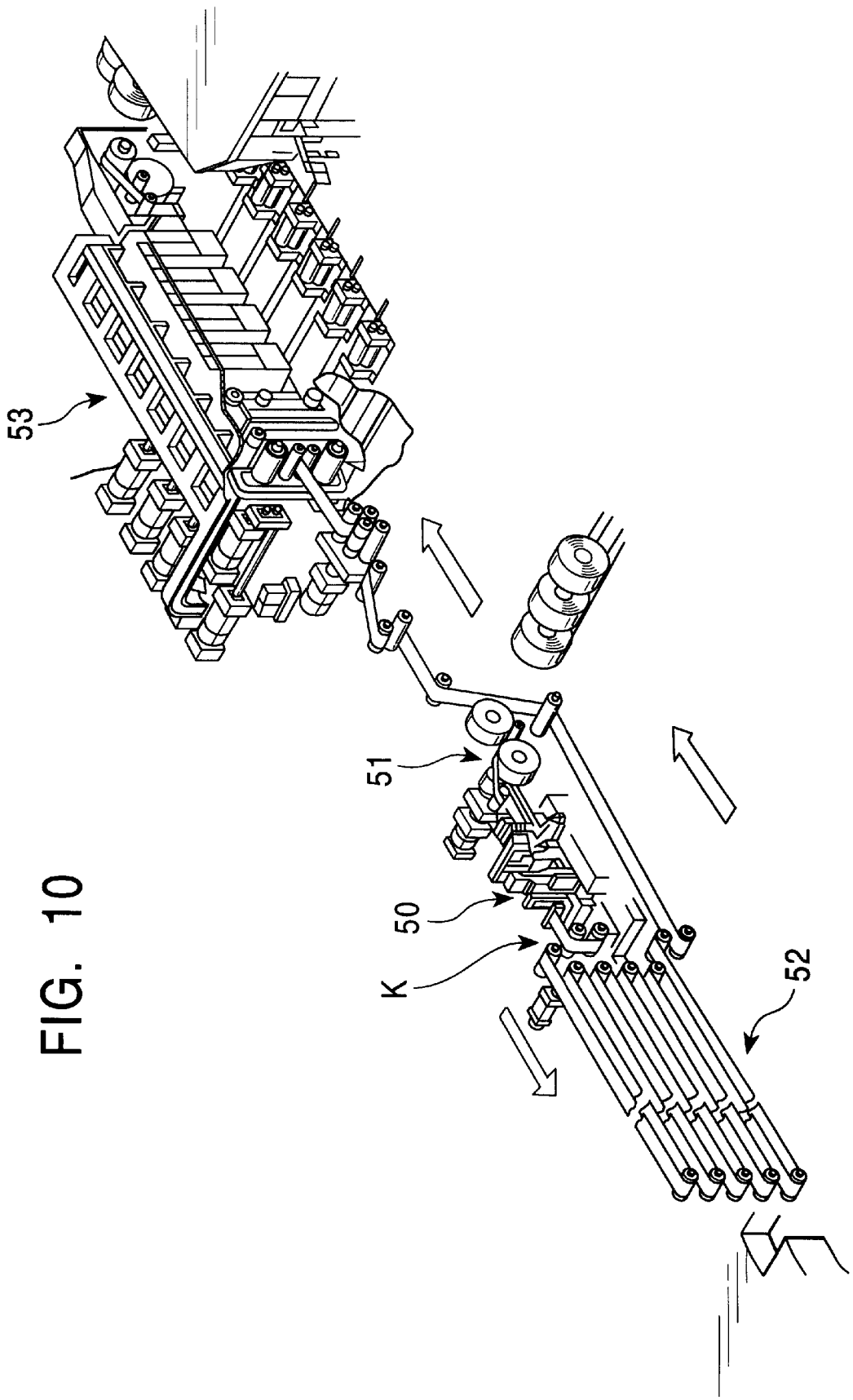
FIG. 10 illustrates typical cold rolling mill and upstream equipment in an embodiment of utilizing the embodiment.

FIG. 10 illustrates a layout of a tandem cold rolling mill. As a second arrangement, it is conceivable to provide the testing equipment (not shown) on the exit side of the welding machine 50 at location K in FIG. 10.

In FIG. 10, the payoff reel 51, a looper 52, and a cold rolling mill 53, are shown.

A third arrangement will now be described. The same reference numerals are assigned to the same component part as in the above-mentioned first form of application, and a detailed description will be omitted.

This third arrangement relates to manufacturing equipment of a hot-rolled steel sheet. In this arrangement, the part up to the pickling process has the same apparatus configuration as in the first form of application. A finishing process is arranged downstream of the pickling process. The configuration comprises: a blast furnace—a converter—(a degassing equipment)—a continuous casting equipment—(slab storage)—hot rolling—a pickling process of hot-rolled steel sheet—a finishing process.

Other configurations, functions and effects are as described for the first arrangement.

According to this arrangement, upon shipping a hot-rolled steel sheet (steel strip 1) as a product, it is possible to detect flaws in the steel sheet at a high reliability, and perform quality control at a high accuracy.

The installing position of the testing equipment is not limited to the pickling process. It may alternatively be provided between the pickling process and the finishing process.

A fourth arrangement will now be described. The same reference numerals are assigned to the same equipment and apparatuses as in the above-mentioned first arrangement, and a detailed description thereof is omitted here.

This arrangement relates to manufacturing equipment of a cold-rolled steel sheet. This form of application has the same equipment configuration as in the first arrangement, and flaws in the hot-rolled steel sheet are detected at a satisfactory reliability as described above using the testing apparatus installed in the pickling process. Carrying out an investigation regarding detected flaws, the sources are discovered for each kind of flaw (shape, size and quantity) on the basis of the result of this investigation (testing information).

For example, when an inclusion (non-metallic inclusion) is to be detected, sources are previously discovered for each kind of inclusion. If the kind of the flaw in question is determined, and the steel-making conditions particularly casting conditions) can be modified so as to eliminate the target flaws. The casting conditions include, for example, the slab casting position, the casting speed, the casting temperature and the flux used, and other steel-making conditions include the oxygen content in the molten steel and the degassing time.

Advantages of the fourth arrangement are as follows: (a) Because testing is carried out before the manufacturing process of the steel sheets branches off various downstream processes, flaws can be detected efficiently. (b) Because testing is carried out in a process near the casting process in which flaws tend to be produced, it is possible to take rapid actions upon detection. Particularly, flaws are intermittently produced in processes such as the casting process, and have different shapes corresponding to the source of flaw. Therefore it is possible to discover the source of flaw by use of testing results on flaw shapes. In this form of application, it is possible to take rapid actions, and avoid the intermittent occurrence of similar types of flaws. (c) Because testing is carried out in a process near the casting process in which flaws tend to be produced, detected flaws are substantially non-deformed and it is possible to discover a source of the flaws with high accuracy. It is easy to take actions on the basis of the testing information as described above.

These advantages will supplementary be described for a steel sheet for a can. In conventional manufacturing equipment of steel sheet for cans, internal flaws are discovered in the inspection after cold rolling, or in the inspection after surface-treatment process, or after passage through these inspections, finally discovered in a production process of cans at customer site.

Even when flaws are found, taking actions requires sampling of flaws, an investigation thereof, and after estimation of a source, reviewing the manufacturing history of the defective product, and discovery of unsatisfactory conditions.

Therefore, it has conventionally taken much time and labor to determine a source of flaws and decide the necessary actions. Thus, many steel sheets manufactured before taking actions are very likely to be defective and classified into a lower grade as a result of rejection, or diverted to another use, thus leading to a loss. Further, in order to make up for the rejected products, it is necessary to rework the production schedule for reproduction, thus causing very serious economic damage.

By applying this form of application to the manufacture of a steel sheet for can, in contrast, it is possible to take necessary counter-measures in an upstream process where defective sheets are still low in number.

Further, with the ultrasonic testing apparatus 30 by use of the ultrasonic line sensor 20, detailed information including not only the position of flaws, but also the shape of flaws, and the size of the flaws is available, thus minimizing the labor for sampling and investigation.

A testing apparatus is provided in the pickling process in this form of application. However, in order to secure the above-mentioned advantages, the testing apparatus may be provided at any position between the end of hot rolling line of the strip and the start of cold rolling line of the strip.

A fifth arrangement will now be described. The same reference numerals are assigned to the same equipment and apparatus as in the fourth arrangement, and a detailed description thereof is omitted here.

The fifth arrangement relates to a manufacturing equipment of a hot-rolled steel sheet. Processes up to the pickling process form the same apparatus configuration as in the fourth arrangement, except that a finishing process is arranged downstream of the pickling process. The configuration comprises: a blast furnace—a converter—(degassing equipment)—continuous casting equipment—(slab storage)—hot rolling—a pickling equipment for hot-rolled steel sheets—a finishing process.

Other configurations, functions and advantages are the same as in the fourth arrangement.

According to the fifth arrangement, when shipping a hot-rolled steel sheet (steel strip 1) as a product, it is possible to rapidly take actions against flaws in steel sheets, thus almost eliminating intermittent production of defective hot coils. As a result, it is possible to improve the yield and quality in the manufacture of hot-rolled steel sheets.

A sixth arrangement will now be described. The same reference numerals are assigned to the same equipment and apparatus as in the above arrangements and a detailed description is omitted here.

This arrangement relates to manufacturing equipment of a cold-rolled steel sheet having the same component equipment as in the first arrangement. This arrangement is suitable for manufacturing steel sheets for cans having strict quality requirements.

In this arrangement, testing is carried out in the pickling process of the steel strip 1 (hot-rolled steel sheet) before the manufacturing process of the steel sheet branches off in various downstream processes, and information on inclusions (eg., size and quantity of inclusions) are obtained simultaneously in flaws detection. The use of the steel sheet tested is determined on the basis of this testing results, the process after cold rolling is selected, or cold rolling conditions are adopted or changed.

According to this arrangement, it is possible to previously determine an appropriate use (destination) in response to the quality level of the steel sheet. In a conventional testing immediately before shipping, even when diverting is required after clarification of the quality level, the steel sheet size or material (hardness or the like) are not suitable for a preferred destination of diverting, and it is often impossible to make a proper diverting. For example, steel sheet for cans is rolled into a thickness of 0.2 mm, and is smaller in thickness compared to other uses. However, in this form of application, it is possible to select appropriate cold rolling conditions and annealing conditions in response to the specification of diverted product and select diverting destination in wide range, thus improving the yield of manufacture of steel sheet. As a result of an enlarged allowance of diversion, deterioration of productivity can be minimized even when imposing more strict evaluation of inclusions for the high-quality materials, thus permitting improvement of quality.

Further, according to this form of application, slabs produced at the start and end of continuous casting (unsteady state slabs) are applicable for steel sheets for can, as well as for improving the yield. In production of cans that have very thin wall thickness, very small internal flaw can be the source of defective can and steel sheet for cans need to contain very few internal flaws. If defective can is discovered in the production line of can, the production line stops and drinks waiting for canning are discarded, thus leading to serious economic damage. Therefore the tolerance of rejectable cans caused by flaws in the material steel sheet for cans is very strict. Conventionally, in order to avoid above-mentioned trouble, unsteady state slabs that are likely to contain many internal flaws cannot be used for steel sheet for cans. By using this arrangement, however, as it is possible to detect internal flaws in the steel sheet made from unsteady state slabs with high reliability, steel sheets not suitable for cans can easily be discovered and diverted to the other uses. As a result, improvement in yield is expected through utilization of unsteady state slabs.

EXAMPLES

Example 1

Figure 6:
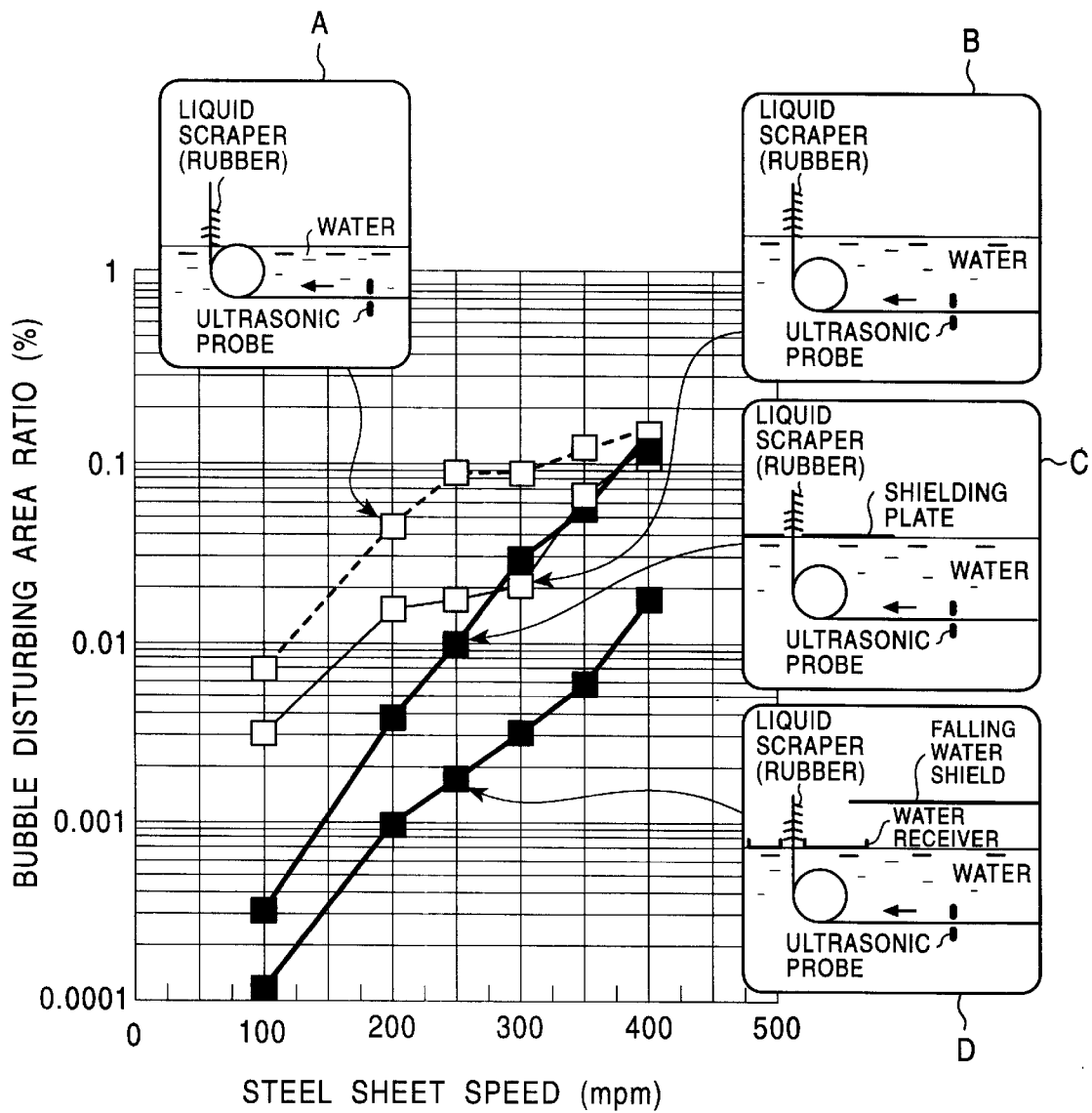
FIG. 6 illustrates the relationship between the steel sheet speed and the bubble interference area ratio.

To investigate the effect of the preferred embodiments of the first aspect of this invention, an experiment was carried out using an experimental apparatus based on the first embodiment. FIG. 6 illustrates the result.

In this example, rubber scrapers were used in place of the wringer roll 15 as the liquid removing device, and was installed at a position about 30–300 mm from the water surface. Hot-rolled steel sheet in the form of an endless belt was circulated (carried) as the steel strip 1.

The bubble interference area ratio was determined for the case of testing by use of an ultrasonic line sensor 20, for the following four cases:

(1) The carrying roll in the water was not fully immersed as a comparative example (reference symbol A in FIG. 6).
(2) The carrying roll in the water was fully immersed with a distance of 5 mm between the liquid surface and the top of the roll (B in FIG. 6).
(3) The carrying roll in the water was fully immersed, and a shielding plate serving as a liquid shielding device was arranged on the water surface (C in FIG. 6). The shielding plate was a flat plate that did not sufficiently catch the dropping water.
(4) The carrying roll in the water was fully immersed, and a container serving as a liquid reservoir was provided at the water surface (D in FIG. 6). The water received in the container was discharged to outside of the liquid tank 4.

The bubble interference area ratio represents the ratio of the cross-sectional area of the ultrasonic beam subjected to interference of air bubbles relative to the total cross-sectional area of the ultrasonic beam.

Air bubbles can be falsely detected because the echo from air bubbles on the upper or back surface of the steel strip 1 has the same path length as the echo from a flaw. Bubble echo with large amplitude is falsely recognized as a flaw echo. It has separately been confirmed that a bubble interference area ratio of within 0.05% permits stable testing with a sensitivity fluctuation within 1 dB while the disturbance of ultrasounds propagation by air bubbles is sufficiently small.

When a slightly larger sensitivity fluctuation is allowed, e.g., within 3 dB, the bubble interference area ratio suffices to be within about 0.1%.

In order to improve the stability of the sensitivity, the bubble interference area ratio should preferably be within about 0.02%.

As is clear from FIG. 6, bubble producing can be significant if the carrying roll in the water is not fully immersed, and in order to ensure stable flaw detection, the steel sheet speed (steel sheet carrying speed) must be up to about 200 m/min. On the other hand, the steel sheet speed can be increased up to about 300 m/min if the carrying roll in the water is fully immersed or shielding plate receiving water dropping from the steel sheet. Further, when a container receiving water dropping from the steel sheet is provided, stable flaw detection is possible even at a steel sheet speed of over about 400 m/min.

When a container-shaped liquid-catching device giving a large shielding effect is used, the bubble interference area ratio is small even at a steel sheet speed of about 400 m/min. Therefore, a sufficient testing sensitivity is ensured at a higher steel sheet speed.

More specifically, by adopting the first embodiment, stable flaw detection can be carried out even by installing a flaw detecting apparatus in a process in which the steel strip is carried at a high speed within a range of from about 400 to about 1,000 m/min.

An experiment was carried out at a steel sheet speed of 900 m/minute for each of the cases B to D in FIG. 6. The resultant value of the bubble interference area ratio were: B: 0.6%, C: 0.5% and D: 0.042%.

When using a hot-rolled steel sheet previously subjected to flattening with a tension leveler, the bubble interference area ratio was reduced by about 20%. For example, a bubble interference area ratio of 0.01% for a steel sheet before flattening was reduced to about 0.008% for the flattened steel sheet.

The bubble interference area ratio was reduced by about 20% also in case C in FIG. 6 where the steel strip was inclined by 20° from the vertical direction.

In case B in FIG. 6, where the total immersion roll depth was 50 mm, not 5 mm, the bubble interference area ratio was reduced by about 10%.

In addition, in the case where the steel strip is carried at a speed within a range of from about 100 to about 200 m/minute, a bubble interference area ratio was largely reduced to about 0.005% by use of the first aspect of this invention. Estimation of the flaw size on the basis of height of the flaw echo can be achieved with high accuracy because no fluctuation of the sensitivity is caused by air bubbles. Therefore, the use of the first aspect of this invention is effective in the case where the steel strip is carried at a speed within a range of from about 100 to about 200 m/minute.

Example 2

An experiment similar to that in Example 1 was carried out at a speed of 150 m/min with the use of a flaw detecting apparatus shown in FIG. 8. As a result, the bubble interference area ratio was satisfactory with a value of about 0.04%.

Example 3

In a manufacturing equipment of cold-rolled steel sheets based on application of the first arrangement to a steel sheet manufacturing line, a testing test was carried out with the above-mentioned testing equipment with a large amount of steel sheets containing about 0.3 inclusions per ton (about 0.005 inclusions per $m^2$) as the sample. As a result, all inclusions were detected.

When testing was carried out without tension imparting by the bridle roll under the above-mentioned conditions, the detection ratio was decreased to about 99.5%. When not using a tension leveler, the detection ratio was reduced to about 99.0%.

For comparison purposes, a steel sheet containing 0.3 inclusions per ton was tested with a conventional magnetic leakage flux testing apparatus in a finishing process immediately before shipping of products. As a result, the flaw detection ratio stayed at a level of from 70 to 80% because small indications could not be discriminated from electric noise.

The flaw detection ratio was determined as the ratio of the detected number of inclusions relative to the total number of inclusions. In an experiment using the first arrangement, it was determined that the total number of inclusions approximately equaled the detailed recognized number of inclusions. This is because even when a cold-rolled steel sheet is manufactured from a portion where a flaw was not found in testing and canned into a DI can, defects in working caused by the inclusion were almost non-existent, and a strict inspection by sampling showed no undetected inclusions.

Example 4

An example in which the fourth arrangement was applied to a steel sheet manufacturing process will be described. The following description is based on an assumption of a steel sheet for cans (a low-carbon Al-killed steel, an ultra-low-carbon steel) as a cold-rolled steel sheet, but is not limited to a steel sheet for cans.

First, for the purpose of permitting rapid actions by feeding back the testing information to the upstream processes, the following investigation and analyses were conducted in advance:

The hot-rolled steel sheet serving as the material for the steel sheet for cans was tested with an ultrasonic testing apparatus 30 arranged on the entry side of a hydrochloric acid pickling tank according to the fourth arrangement. Samples of steel sheet were taken from the position where a flaw was detected in testing. Cross sections in the rolling direction and the transverse direction were examined with a microscope, and the kind of flaw and the process in which the flaw formed were analyzed. The following three kinds of flaws were classified: (a) non-metallic inclusions including slivers produced during steel-making—continuous casing; (b) scale mark (JIS J TR009-1980, Japan Inst. of Iron & Steel) and scab produced during hot rolling; and (c) gouges formed after hot finish rolling.

For each kind of flaw, the shape of the flaw, its size, and position in the width direction and the longitudinal direction in the steel strip were investigated, and combinations of the result of investigation (classification) of flaws and actions to be taken were worked out into a process standard.

Further, the following analyses were performed for the most important non-metallic inclusions (a).

The tolerance of rejectable cans caused by flaws in the material steel sheet for cans is very strict, as shown in TABLE 1. Particularly, the lower limit for the rejectable can occurrence ratio, which has conventionally been about 100 ppm, must now further be minimized and a rejectable can occurrence ratio of about 10 ppm is now needed.

TABLE 1

| | Manufacturing 2-piece can with 0.17 mm thickness | |
|---|---|---|
| Reject ratio (ppm) | Rejects per 10 tons (cans/10 tons) | Rejects per unit area of steel sheet (cans/m$^2$) |
| 1000 | 300 | 0.04 |
| 100 | 30 | 0.004 |
| 10 | 3 | 0.0004 |

A continuously cast slab for steel sheet for cans manufactured while controlling the casting conditions so as to prevent the occurrence of inclusions as far as possible was hot-rolled and finished into a thickness of 1.8 mm. This hot-rolled steel sheet was tested with an ultrasonic testing apparatus 3 arranged on the entry side of a hydrochloric acid pickling tank according to the fourth arrangement. A steel sheet sample was taken at the position where a flaw was detected in the testing. The cross section of the sample was microscopically observed to examine the position of presence (depth), shape and size of non-metallic inclusions. Further, the non-metallic inclusions were subjected to an EPMA analysis to examine the chemical composition. Sources were clarified by collating the result of investigation with the continuous casting conditions.

Appropriate actions were taken against each source, and an inspection was carried out again with the testing apparatus 30 to examine the appropriateness of clarified sources and actions taken. For samples for which the sources and actions were ascertained, the relationship with the testing information was classified again.

Figure 11:
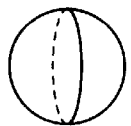
FIG. 11 illustrates a classification of non-metallic inclusions.
Figure 11:
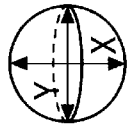
Figure 11:
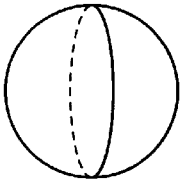
Figure 11:
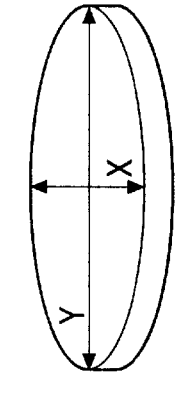
Figure 11:
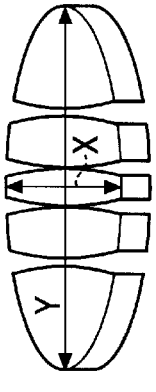
Figure 11:

Many cases of such studies were repeated, and classified. As a result, kinds of inclusions could be classified into the types A to C as shown in FIG. 11, and it is clarified that each type has relation to its shape at the stage of the slab.

Non-metallic inclusions of type A are detected as a sphere having a diameter (X, Y) within a range of from 30 to 50 $\mu$u after hot rolling.

The type-A inclusions are made of $Al_2O_3$, and show the highest constitution ratio of about 70% of the total inclusions. Because of their extra-high hardness, these inclusions are never broken through hot rolling, cold rolling or temper rolling in the manufacture of steel sheets, or ironing, stretch-draw forming, or stretch-ironing forming in production of cans, and are never deformed. Because the type-A inclusions retain their shape upon mixing in the slab, pinholes or micro-cracks at necked-in forming are produced at a strong probability when worked in canning to a thickness of about 40 to 100 $\mu$m.

Some type-A inclusions are deoxidation products formed in the Al deoxidation process applied in the converter or a vacuum degassing conducted thereafter. Even after deoxidation, supply of oxides in the molten steel or on the molten steel surface causes oxidation of Al remaining in an amount of at least 0.01 wt. % in steel (reoxidation) and type-A inclusions, which are $Al_2O_3$ inclusions, increase in number.

For example, if converter slag remains in the molten steel (residual slag itself forms a type-B inclusion as described later), reoxidation of the residual slag which acts as a deoxidizer of iron oxides leads to an increase of type-A inclusions. Particularly, in low-carbon, Al-killed molten steel, the slag contains so many iron oxides that shows a high fluidity. As a result, slag tends to flow out into the ladle upon tapping from the converter, and is mixed with molten steel.

In the continuous casing process carried out by shutting off the open air, type-A inclusions increase owing to reoxidation when the air leaks in.

At the time of formation, $Al_2O_3$ inclusions are as small in size as several microns in diameter, and are not so harmful. They, however, become coarser through aggregation and gathering and can grow in size to about 30 to 50 $\mu$m in the steel-making process.

From the above-mentioned result of study, when type-A inclusions are detected, steel-making conditions are corrected so as to reduce the amount of oxygen in the molten steel upon tapping, and to reduce the amount of deoxidation products. The decrease of deoxidation products can be examined by analyzing the ratio of the soluble (soluble in acid) Al content relative to the weight of metallic Al added to the molten steel. Insoluble (insoluble in acid) Al has become $Al_2O_3$ inclusions. The steel-making conditions are modified so as to achieve a soluble Al ratio of, for example, at least 25%.

Examination of the instruments to detect leaking in of the open air caused by insufficient shut-off in the continuous casting process or the like is also effective as a countermeasure. Further, thoroughgoing check of the outputs of the slag detector to detect the amount of mixed slag is also effective as an action.

Apart from Al-killed steel, Si-killed, Ti-killed and steels based on combinations of these are used at present. In these steels, A-type $Al_2O_3$ inclusions decrease, and B-type and C-type inclusions increase.

Non-metallic inclusions of type B are detected as flat and substantially oval shape having a longer diameter Y of from 100 to 300 $\mu$m and a shorter diameter X of from 50 to 150 $\mu$m after hot rolling.

Type-B inclusions are made of $CaO$—$Al_2$—$O_3$, and the constitution ratio is low as about 20% of the total inclusions in general. However, because of their hardness, these inclusions are not cut off even through hot rolling, cold rolling or temper rolling in the manufacture of steel sheets or ironing, stretch-draw forming or stretch ironing forming in production of cans, and are elongated. As a result, flange cracks are produced at a high probability during working to about the thickness of 100 $\mu$m in production of cans.

Type-B inclusions comprising converter slag mixed finely in molten steel, or tundish flux mixed in the same manner, is deoxidized by Al in molten steel and integrally combines with $Al_2O_3$ of deoxidation products through aggregation and gathering.

Based on the above-mentioned results of the study, when type-B inclusions are detected, actions should preferably be taken to reduce generation of $Al_2O_3$ and mixing of slag as in type-A inclusions. To avoid mixing of tundish flux, improvement can be achieved by checking the position of the refractory nozzle for injecting molten steel into the tundish, and setting the nozzle position to a suitable position thereafter.

Non-metallic inclusions of type C are detected in a substantially oval disk-like shape having a longer diameter Y of at least 300 $\mu$m and a shorter diameter X of at least 150 $\mu$m and tom in several pieces after hot rolling in general. Type-C inclusions are made of $CaO$—$SiO_2$—$Al_2O_3$, and its constitution ratio is low, such as about 10% of the total inclusions. Because this inclusion is rather soft, it is deformed, elongated and torn in several pieces through hot rolling, cold rolling, temper rolling in the manufacture of steel sheets, or ironing, stretch-draw forming or stretch ironing forming in production of cans. Although the probability of occurrence of flaws is low, breakage of the drum wall is caused during working to a thickness of up to 100 $\mu$m in production of cans. Because drum breakage makes it impossible to continue production of cans unless the defective can is removed, it results in stoppage of the production line and largely impairs productivity. In spite of a low probability of occurrence of rejects, therefore, it is desirable to take actions against type-C inclusions.

Type-C inclusions are formed as a result of integration of mold flux finely mixed in molten steel with $Al_2O_3$ as deoxidation products through aggregation and gathering. To judge from the above-mentioned result of the study, when type-C inclusions are detected, it is desirable to take actions so as to reduce generation of $Al_2O_3$ as in type-A inclusions. The problem may be solved by reducing fluctuations of the metal surface level by use of a mold metal surface position controller.

In this example based on the application of the fourth arrangement to the steel sheet manufacturing line, it is determined what type of inclusion (A to C) the current flaw is classified and the extent of production on the basis of the testing results obtained by the testing apparatus arranged in the pickling process. Actions appropriate for each type of inclusion are taken as described above. As a result, it is possible to take appropriate counter-measures to reduce or eliminate the flaw immediately, rapidly and largely reduce occurrence of defective product coils, improve the yield, and largely reduce the reject ratio.

In the above-mentioned examples, inclusions which are formed depending upon steel-making and casting conditions are tested, and on the basis of this testing information, the process conditions for the steel-making and casting process are modified for rapid solution. Application of the present invention is not however limited to this.

For example, for a flaw formed in hot rolling, falling under the classification (b), it is possible to previously classify, on the basis of the shape, the relations between the hot rolling conditions (heating, cooling and rolling conditions) and the shape of the detected flaw (scale mark, scab) as in the above-mentioned case. In this case, it is desirable to conduct testing of flaws in the steel strip 1 (hot-rolled steel sheet) by the use of testing equipment provided at the upstream side of a cold rolling mill, as shown in the second arrangement. On the basis of the testing information of the flaw formed in the hot rolling, rapid actions can be taken by modifying the hot rolling conditions by feeding back the information to the hot rolling process.

Example 5

Upon application of the sixth arrangement to a steel sheet manufacturing line, cold-rolled steel sheets were previously classified into destination ranks 1 to 6 shown in TABLE 2 in response to the tolerable extent (average number per m$^2$) of inclusions. Inclusion were detected by the use of an ultrasonic testing apparatus 30 in the pickling process, and when the extent of inclusions did not satisfy the standard of the proposed use, the destination was changed on the basis of TABLE 2.

TABLE 2

| Number of inclusions (per m²) | Ranking (order) | Applied to | | Product Specifications | | |
|---|---|---|---|---|---|---|
| | | | | | Thickness (mm) (upon shipment) | Class (hardness) |
| Up to 0.001 | 1 | 2-piece can | Drink can, Food can | Positive-pressure can | 0.16 to 0.26 | T3 to DR8 |
| Up to 0.005 | 2 | 2-piece can | Drink can, Food can | Negative-pressure can | 0.16 to 0.26 | T2 to DR9 |
| Up to 0.01 | 3 | 3-piece can | Drink can, Food can. | Negative-pressure can | 0.15 to 0.24 | T2 to T5 |
| Up to 0.05 | 4 | 3-piece can | General can | Negative-pressure can | 0.2 to 0.3 | T2 to T3 |

TABLE 2-continued

| Number of inclusions (per m$^2$) | Ranking (order) | Applied to | | | Product Specifications | |
|---|---|---|---|---|---|---|
| | | | | | Thickness (mm) (upon shipment) | Class (hardness) |
| Up to 0.1 | 5 | 3-piece can | 18L can | Negative-pressure can | 0.3 to 0.4 | T3 to T4 |
| No regulation | 6 | 3-piece can | Pail can | Negative-pressure can | 0.4 to 0.5 | T3 to T4 |

In TABLE 2, the two-piece can is made from a steel sheet to be subjected to drawing (drawing, deep-drawing) by the can maker after shipment, into a can thickness of about 0.1 mm. The three-piece can is made of a steel sheet formed directly into a can through cylindrical working and welding, and the wall thickness of the can is substantially the same as that of the sheet steel. The positive-pressure can is used with a high interior pressure, containing a carbonated drink, and has a small can thickness. The negative-pressure can is subjected, after vacuum packing, to sterilization, and used with an inner pressure of less than atmospheric pressure. The can thickness is therefore slightly larger. There are product grades T1 to T6, and DR8 to DR10, with a larger number indicating a higher hardness.

A steel sheet with DR notation has a hardness increased through a secondary cold rolling (a cold reduction of from several % to several tens of %) in place of the temper rolling (slight cold reduction of about 1% for adjustment of hardness and shape) after annealing.

When changing the destination, various conditions, such as the cold reduction of the primary cold rolling, the annealing temperature, and the cold reduction of temper rolling or the secondary cold rolling, were determined in response to the product specifications as shown in TABLE 2. It is also possible to change hardness from the initially planned values by varying the annealing temperature or the cold reduction of the temper rolling (or the secondary cold rolling). However, change in destination (diversion) should preferably be made within the same hardness class, if possible. The chemical composition may be different, in addition to the hardness class; the different composition may lead to a possibility that an appropriate material properties besides hardness are not available.

Cases of diversion will now be described.

Diversion 1: A hot-rolled steel sheet initially planned to be applied for a steel sheet for cans, rank 3, T4 class (thickness: 0.20 mm) was tested in the pickling line, and 0.025 inclusions/m$^2$ were detected on the average. With reference to the order entry, it was decided to divert this steel sheet to rank 4, T3 class (thickness: 0.20 mm). Upon diversion, no change was made in the production lines such as cold rolling, annealing and temper rolling, and condition such as the cold reduction. However, because of a change in hardness class, the annealing temperature was increased by 30° C., and the cold reduction for temper rolling (specified by elongation) was reduced by 0.3%.

Diversion 2: A hot-rolled steel sheet initially planned to be applied for a steel sheet for cans, rank 1, T5 class (thickness: 0.25 mm) was tested in the pickling line, and 0.03 inclusions/m$^2$ were detected on the average. With reference to the order entry, therefore, it was decided to divert this steel sheet to rank 2, DR9 class (thickness: 0.16 mm). While the initially planed annealing line comprised an integrated line containing a continuous annealing furnace and a temper rolling mill, this was modified into an integrated line of a continuous annealing furnace and a DR rolling mill upon this diversion. The cold reductions and the annealing temperature were also changed to meet the target material.

Application of the sixth arrangement resulted in an improvement of the yield and an increase in the amount of steel sheet as products by 20% as a whole.

According to the flaw detecting method and apparatus of the present invention, as described above, in testing a strip continuously carried, the disturbance of air bubbles is largely reduced. Even at a high carrying speed of the strip, the invention provides stable flaw detection.

In addition to these advantages, the simple apparatus configuration permits reduction of the number of parts and eliminates the necessity of a larger-scale apparatus. As a result, it is possible to achieve a low equipment cost and easy maintenance.

By adopting the invention, as described above, it is possible to detect flaws in a cold-rolled steel sheet and a hot-rolled steel sheet at a high reliability.

Furthermore, because the investigation of a source of flaw is easier, it is possible to rapidly take actions to avoid the production of such flaws. This improves the yield of cold rolled sheets and hot-rolled sheets, and permits improvement of quality of steel sheets.

When shipping a hot-rolled steel sheet as an intermediate product in manufacturing equipment of cold-rolled steel sheets, the invention permits sufficient quality control.

Further, in the manufacture of cold-rolled steel sheets, flaws can be detected in testing at a single location, thus permitting simplification of the testing equipment. Because of the possibility to obtain the information on quality level of each steel sheet before cold rolling, it is possible to direct the individual steel sheets to appropriate cold rolling lines. Therefore, scrap is reduced, with an improvement of the cold-rolled steel sheet yield and improvement of quality of steel sheets.

The method of the invention, if adopted in a process for other metal sheet, such as an Al or Cu strip, displays similar advantages.

What is claimed is:

1. A method of detecting defects in a strip, comprising;
    continuously testing a strip by use of ultrasound as the strip is carried continuously through a liquid in which the strip is fully immersed; and
    inhibiting the formation of air bubbles in the liquid during carrying of the strip through the liquid by preventing liquid that adheres to the strip and that is carried from the liquid to above the liquid surface from dropping back onto the liquid surface.

2. The method according to claim 1, further comprising:
    carrying the strip at a speed within a range of from about 100 to about 1,000 m/min; and testing the strip in the liquid while carrying the strip by at least one carrying roll in the liquid;

wherein the testing includes inhibiting the generation of air bubbles in the liquid by (i) fully immersing each of the at least one carrying roll into the liquid, and (ii) preventing the liquid that adheres to the strip and that is carried from the liquid to above the liquid surface from dropping back onto the liquid surface.

3. The method according to claim 1, further comprising:

carrying the strip at a speed within a range of from about 100 to about 1000 m/min; and testing the strip in the liquid while carrying the strip by at least one carrying roll in the liquid;

wherein the testing includes inhibiting the generation of the air bubbles in the liquid by (i) fully immersing each of the at least one carrying roll into the liquid, and (ii) upon carrying the strip from the liquid to above the liquid surface, causing the moving direction of the strip to incline relative to a normal to the liquid surface, and (iii) preventing the liquid that adheres at least to the back surface of the strip and is carried from the liquid to above the liquid surface from dropping back onto the liquid surface.

4. The method of claim 1, further comprising:

carrying the strip at a speed within a range of from about 100 to about 1000 m/min; and testing the strip while carrying the strip using at least one carrying roll in the liquid;

wherein the testing includes inhibiting the generation of air bubbles in the liquid by fully immersing each of the at least one carrying roll into the liquid such that a top of each carrying roll is immersed in the liquid to a depth of at least about 5 mm below the liquid surface.

5. The method of claim 2, further comprising inhibiting the generation of the air bubbles in the liquid by removing the liquid, that adheres to the strip and that is carried from the liquid to above the liquid surface, in the proximity of the liquid surface.

6. The method of claim 2, further comprising inhibiting the generation of the air bubbles in the liquid, upon carrying the strip from above the liquid surface into the liquid, by adjusting the moving direction of the strip so that the moving direction is at least substantially perpendicular to the liquid surface.

7. The method of claim 1, wherein the inhibiting of the generation of the air bubbles in the liquid comprises carrying the strip at a speed of less than about 200 m/min.

8. The method of claim 2, further comprising flattening the strip prior to carrying the strip into the liquid.

9. The method according to claim 2, further comprising applying tension to the strip in the moving direction of the strip during passage of the strip through the liquid.

10. The method of claim 1, wherein the strip is metallic.

11. The method of claim 1, wherein the testing is performed in pickling equipment for pickling a hot-rolled steel strip.

12. The method of claim 1, wherein the testing is performed upstream of a cold rolling mill for the strip.

13. A method of manufacturing a cold-rolled steel sheet, comprising detecting a flaw in a steel strip by the method according to claim 1 after hot rolling the strip and prior to cold rolling the strip.

14. An apparatus for continuously testing for defects in a continuously carried strip, comprising:

a liquid;

at least one carrying roll through which the strip is introduced to pass the strip through the liquid such that the strip is fully immersed in the liquid;

an ultrasonic testing apparatus that tests a portion of the strip that is fully immersed in the liquid; and a device that inhibits the formation of air bubbles in the liquid during carrying of the strip through the liquid by preventing liquid that adheres to the strip and that is carried from the liquid to above the liquid surface from dropping back onto the liquid surface.

15. Pickling equipment for pickling a hot-rolled steel strip comprising an apparatus according to claim 14.

16. An apparatus for continuously testing for defects in a continuously carried strip, comprising:

a liquid;

at least one carrying roll through which the strip is introduced to cause the strip to pass through the liquid such that the strip is fully immersed in the liquid;

an ultrasonic testing apparatus that tests a portion of the strip that is fully immersed in the liquid;

wherein each of the at least one carrying roll that is in contact with the liquid is fully immersed in the liquid; and a device that prevents the liquid that adheres to the strip and that is carried from the liquid to above the liquid surface from dropping back onto the liquid surface.

17. An apparatus for continuously testing for defects in a continuously carried strip, comprising:

a liquid;

at least one carrying roll through which the strip is introduced to cause the strip to pass through the liquid such that the strip is fully immersed in the liquid;

an ultrasonic testing apparatus for testing a portion of the strip that is fully immersed in the liquid;

wherein each of the at least one carrying roll that is in contact with the liquid is fully immersed in the liquid;

a device that catches the liquid that drops from a portion of the strip located above the liquid surface to prevent the liquid from dropping back onto the liquid surface; and a device disposed near the liquid surface that removes the liquid that adheres to the portion of the strip that has moved from the liquid to above the liquid surface.

18. A method of detecting defects in a strip, comprising;

continuously testing a strip by use of ultrasound as the strip is carried continuously through a liquid in which the strip is fully immersed, the ultrasonic testing comprising:

arranging a transmitting probe and a receiving probe face to face in the thickness direction of the strip with the strip between the transmitting probe and receiving probe;

transmitting a line-focused ultrasonic beam with the transmitting probe; and receiving an ultrasound reflected at an internal flaw in the strip with the receiving probe, thereby detecting the internal flaw in the strip; and inhibiting the formation of air bubbles in the liquid during carrying of the strip through the liquid.

19. The method of claim 18, wherein the ultrasonic beam (i) enters a first surface of the sheet, (ii) is reflected by the internal flaw to reach the first surface, and (iii) is reflected by the first surface to exit a second surface of the sheet opposite to the first surface.

20. The method of claim 18, wherein the ultrasonic beam (i) enters a first surface of the sheet, (ii) is reflected by a second surface of the sheet opposite to the first surface to reach the internal flaw, and (iii) is reflected by the internal flaw to exit the second surface of the sheet.

* * * * *